(12) United States Patent
Karin et al.

(10) Patent No.: US 8,211,852 B2
(45) Date of Patent: Jul. 3, 2012

(54) MOLECULES AND METHODS OF USING SAME FOR TREATING CCR5/CCR5 LIGANDS ASSOCIATED DISEASES

(75) Inventors: Nathan Karin, Haifa (IL); Gizi Wildbaum, Kiryat Yam (IL)

(73) Assignee: Rappaport Family Institute for Research in the Medical Sciences, Haifa (IL)

( * ) Notice: Subject to any disclaimer, the term of this patent is extended or adjusted under 35 U.S.C. 154(b) by 705 days.

(21) Appl. No.: 12/224,053

(22) PCT Filed: Feb. 18, 2007

(86) PCT No.: PCT/IL2007/000219
§ 371 (c)(1),
(2), (4) Date: Aug. 15, 2008

(87) PCT Pub. No.: WO2007/094005
PCT Pub. Date: Aug. 23, 2007

(65) Prior Publication Data
US 2010/0227805 A1    Sep. 9, 2010

Related U.S. Application Data

(60) Provisional application No. 60/789,920, filed on Apr. 7, 2006, provisional application No. 60/774,191, filed on Feb. 17, 2006.

(51) Int. Cl.
*A61K 38/19* (2006.01)
*C07H 21/00* (2006.01)
*C07K 14/52* (2006.01)

(52) U.S. Cl. ....... 514/1.1; 530/350; 530/402; 536/23.51

(58) Field of Classification Search .................. None
See application file for complete search history.

(56) References Cited

U.S. PATENT DOCUMENTS 6,388,055 B1 * 5/2002 Bergsma et al. ............. 530/350
7,638,299 B2 * 12/2009 Cho et al. .................... 435/69.1
2003/0166024 A1 * 9/2003 Rosen et al. ................. 435/7.23

FOREIGN PATENT DOCUMENTS
WO    WO 2005/106489    11/2005

OTHER PUBLICATIONS

Golding et al. "CCR5 N-Terminal Region Plays a Critical Role in HIV-1 Inhibition by Toxoplasma Gondii-Derived Cyclophilin-18", The Journal of Biological Chemistry, 280(33): 29570-29577, 2005. Abstract, Table 1.
Misumi et al. "Effects of Immunization With CCR5-Based Cycloimmunogen on Simian/HIVSF162P3 Challenge", Journal of Immunology, 176(1): 463-471, 2006. Abstract, p. 463, r-h col., Last §—p. 464, l-h col., § 1.
Platt et al. "Variants of Human Immunodeficiency Virus Type 1 That Efficiently Use CCR5 Lacking the Tyrosine-Sulfated Amino Terminus Have Adaptive Mutations in Gp120, Including Loss of a Functional N-Glycan", Journal of Virology, 79(7): 4357-4368, 2005. Abstract, p. 4358, r-h col., § 3.
Tsimanis et al. "Soluble Chemokine CCR5 Receptor is Present in Human Plasma", Immunology Letters, 96(1): 55-61, 2005.
Wu et al. "Construction, Purification, and Immunogenicity of Recombinant Cystein-Cystein Type Chemokine Receptor 5 Vaccine", Protein Expression and Purification, 49(1): 108-113, 2006. Abstract, p. 109, l-h col., § 3—r-h col., § 1.

* cited by examiner

*Primary Examiner* — Elizabeth C Kemmerer
*Assistant Examiner* — Regina M Deberry
(74) *Attorney, Agent, or Firm* — John P. White; Cooper & Dunham LLP

(57) ABSTRACT

Soluble molecules are provided. Thus, for example, provided is a soluble molecule which comprises a heterologous amino acid sequence conjugated to a CCR5 amino acid sequence being capable of binding a CCR5 ligand, and wherein the molecule is devoid of an N-terminus domain of CCR5. Also provided are pharmaceutical compositions which comprise the above molecules and methods and uses of same.

5 Claims, 10 Drawing Sheets
(9 of 10 Drawing Sheet(s) Filed in Color)

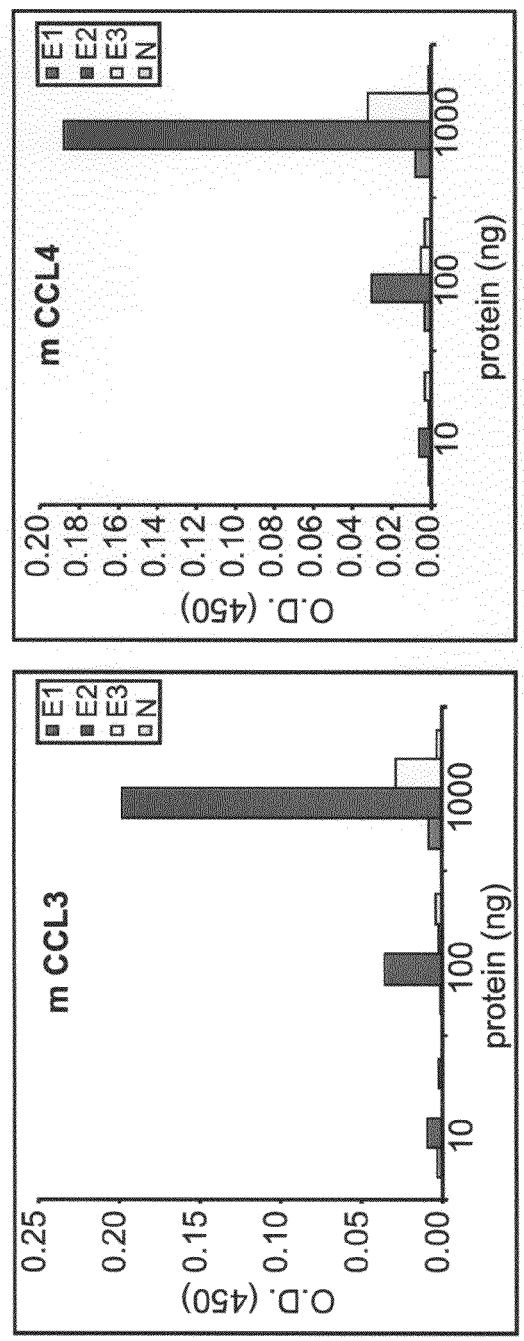
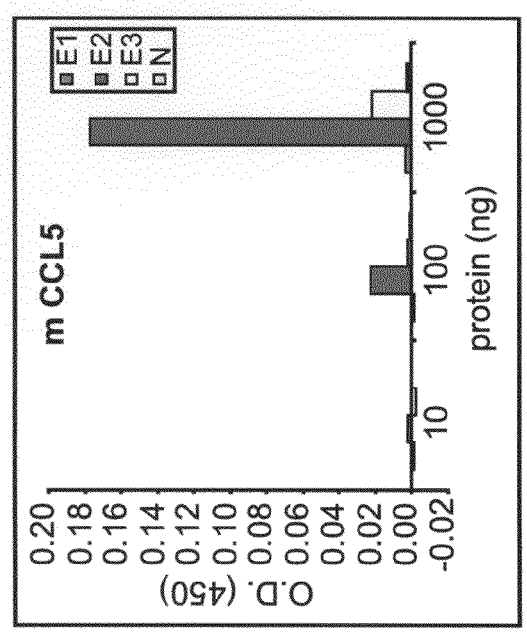
Fig. 2a
Fig. 2b
Fig. 2c

```
                          SEQUENCE LISTING

<160> NUMBER OF SEQ ID NOS: 42

<210> SEQ ID NO 1
<211> LENGTH: 951
<212> TYPE: DNA
<213> ORGANISM: Artificial sequence
<220> FEATURE:
<223> OTHER INFORMATION: Mouse CCR5(EC2)-IgG1 construct coding sequence

<400> SEQUENCE: 1
atggagacag acacactcct gctatgggta ctgctgctct gggttccagg ttccactggt      60
gacgcggccc agccggccag gcgcgcgcgc cgtacgaagc ttagatctca gaaagaaggt     120
tttcattata catgcagtcc tcattttcca cacactcagt atcatttctg gaagagtttc     180
caaacattaa agctcgaggt gcccagggat tgtggttgta agccttgcat atgtacagtc     240
ccagaagtat catctgtctt catcttcccc ccaaagccca aggatgtgct caccattact     300
ctgactccta aggtcacgtg tgttgtggta gacatcagca aggatgatcc cgaggtccag     360
ttcagctggt ttgtagatga tgtggaggtg cacacagctc agacgcaacc ccgggaggag     420
cagttcaaca gcactttccg ctcagtcagt gaacttccca tcatgcacca ggactgcctc     480
aatggcaagg agttcaaatg cagggtcaac agtgcagctt ccctgccccc catcgagaaa     540
accatctcca aaaccaaagg cagaccgaag gctccacagg tgtacaccat tccacctccc     600
aaggagcaga tggccaagga taaagtcagt ctgacctgca tgataacaga cttcttccct     660
gaagacatta ctgtggagtg gcagtggaat gggcagccag cggagaacta caagaacact     720
cagcccatca tggacacaga tggctcttac ttcgtctaca gcaagctcaa tgtgcagaag     780
agcaactggg aggcaggaaa tacttttcacc tgctctgtgt tacatgaggg cctgcacaac     840
caccatactg agaagagcct ctcccactct cctggtaaag ggcccgaaca aaaactcatc     900
tcagaagagg atctgaatag cgccgtcgac catcatcatc atcatcattg a             951

<210> SEQ ID NO 2
<211> LENGTH: 316
<212> TYPE: PRT
<213> ORGANISM: Artificial sequence
<220> FEATURE:
<223> OTHER INFORMATION: Mouse CCR5(EC2)-IgG1 polypeptide

<400> SEQUENCE: 2

Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Arg Arg Thr
            20                  25                  30

Lys Leu Arg Ser Gln Lys Glu Gly Phe His Tyr Thr Cys Ser Pro His
        35                  40                  45

Phe Pro His Thr Gln Tyr His Phe Trp Lys Ser Phe Gln Thr Leu Lys
    50                  55                  60

Leu Glu Val Pro Arg Asp Cys Gly Cys Lys Pro Cys Ile Cys Thr Val
```

```
                65                  70                  75                  80
Pro Glu Val Ser Ser Val Phe Ile Phe Pro Lys Pro Lys Asp Val
                    85                  90                  95

Leu Thr Ile Thr Leu Thr Pro Lys Val Thr Cys Val Val Asp Ile
                100                 105                 110

Ser Lys Asp Asp Pro Glu Val Gln Phe Ser Trp Phe Val Asp Val
            115                 120                 125

Glu Val His Thr Ala Gln Thr Gln Pro Arg Glu Glu Phe Asn Ser
        130                 135                 140

Thr Phe Arg Ser Val Ser Glu Leu Pro Ile Met His Gln Asp Cys Leu
145                 150                 155                 160

Asn Gly Lys Glu Phe Lys Cys Arg Val Asn Ser Ala Ala Phe Pro Ala
                165                 170                 175

Pro Ile Glu Lys Thr Ile Ser Lys Thr Lys Gly Arg Pro Lys Ala Pro
                180                 185                 190

Gln Val Tyr Thr Ile Pro Pro Lys Glu Gln Met Ala Lys Asp Lys
            195                 200                 205

Val Ser Leu Thr Cys Met Ile Thr Asp Phe Phe Pro Glu Asp Ile Thr
210                 215                 220

Val Glu Trp Gln Trp Asn Gly Gln Pro Ala Glu Asn Tyr Lys Asn Thr
225                 230                 235                 240

Gln Pro Ile Met Asp Thr Asp Gly Ser Tyr Phe Val Tyr Ser Lys Leu
                245                 250                 255

Asn Val Gln Lys Ser Asn Trp Glu Ala Gly Asn Thr Phe Thr Cys Ser
                260                 265                 270

Val Leu His Glu Gly Leu His Asn His His Thr Glu Lys Ser Leu Ser
            275                 280                 285

His Ser Pro Gly Lys Gly Pro Glu Gln Lys Leu Ile Ser Glu Glu Asp
        290                 295                 300

Leu Asn Ser Ala Val Asp His His His His His
305                 310                 315

<210> SEQ ID NO 3
<211> LENGTH: 966
<212> TYPE: DNA
<213> ORGANISM: Artificial sequence
<220> FEATURE:
<223> OTHER INFORMATION: Human CCR5(EC2)-IgG1 construct coding sequence

<400> SEQUENCE: 3
atggagacag acacactcct gctatgggta ctgctgctct gggttccagg ttccactggt      60
gacgcggccc agccggccag gcgcgcgcgc cgtacgaagc ttatctttac cagatctcaa    120
aaagaaggtc ttcattacac ctgcagctct cattttccat acagtcagta tcaattctgg    180
aagaatttcc agacactcga gcccaaatct tgtgacaaaa ctcacacatg cccaccgtgc    240
ccagcacctg aactcctggg gggaccgtca gtcttcctct tccccccaaa acccaaggac    300
accctcatga tctcccggac ccctgaggtc acatgcgtgg tggtggacgt gagccacgaa    360
gaccctgagg tcaagttcaa ctggtacgtg gacggcgtgg aggtgcataa tgccaagaca    420
aagccgcggg aggagcagta caacagcacg taccgtgtgg tcagcgtcct caccgtcctg    480
caccaggact ggctgaatgg caaggagtac aagtgcaagg tctccaacaa agccctccca    540
gcccccatcg agaaaaccat ctccaaagcc aagggcagcc ccgagaacca caggtgtac    600 accctgcccc catcccggga ggagatgacc aagaaccagg tcagcctgac ctgcctggtc    660
aaaggcttct atcccagcga catcgccgtg gagtgggaga gcaatgggca gccggagaac    720
```

```
aactacaaga ccacgcctcc cgtgctggac tccgacggct ccttcttcct ctatagcaag    780
ctcaccgtgg acaagagcag gtggcagcag gggaacgtct tctcatgctc cgtgatgcat    840
gaggctctgc acaaccacta cacgcagaag agcctctccc tgtccccggg taaagggccc    900
gaacaaaaac tcatctcaga agaggatctg aatagcgccg tcgaccatca tcatcatcat    960
cattga                                                              966
```

<210> SEQ ID NO 4
<211> LENGTH: 321
<212> TYPE: PRT
<213> ORGANISM: Artificial sequence
<220> FEATURE:
<223> OTHER INFORMATION: Human CCR5(EC2)-IgG1 polypeptide

<400> SEQUENCE: 4

```
Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Arg Arg Thr
            20                  25                  30

Lys Leu Ile Phe Thr Arg Ser Gln Lys Glu Gly Leu His Tyr Thr Cys
        35                  40                  45

Ser Ser His Phe Pro Tyr Ser Gln Tyr Gln Phe Trp Lys Asn Phe Gln
    50                  55                  60

Thr Leu Glu Pro Lys Ser Cys Asp Lys Thr His Thr Cys Pro Pro Cys
65                  70                  75                  80

Pro Ala Pro Glu Leu Leu Gly Gly Pro Ser Val Phe Leu Phe Pro Pro
                85                  90                  95

Lys Pro Lys Asp Thr Leu Met Ile Ser Arg Thr Pro Glu Val Thr Cys
            100                 105                 110

Val Val Val Asp Val Ser His Glu Asp Pro Glu Val Lys Phe Asn Trp
        115                 120                 125

Tyr Val Asp Gly Val Glu Val His Asn Ala Lys Thr Lys Pro Arg Glu
    130                 135                 140

Glu Gln Tyr Asn Ser Thr Tyr Arg Val Val Ser Val Leu Thr Val Leu
145                 150                 155                 160

His Gln Asp Trp Leu Asn Gly Lys Glu Tyr Lys Cys Lys Val Ser Asn
                165                 170                 175

Lys Ala Leu Pro Ala Pro Ile Glu Lys Thr Ile Ser Lys Ala Lys Gly
            180                 185                 190

Gln Pro Arg Glu Pro Gln Val Tyr Thr Leu Pro Pro Ser Arg Glu Glu
        195                 200                 205

Met Thr Lys Asn Gln Val Ser Leu Thr Cys Leu Val Lys Gly Phe Tyr
    210                 215                 220

Pro Ser Asp Ile Ala Val Glu Trp Glu Ser Asn Gly Gln Pro Glu Asn
225                 230                 235                 240

Asn Tyr Lys Thr Thr Pro Pro Val Leu Asp Ser Asp Gly Ser Phe Phe
                245                 250                 255

Leu Tyr Ser Lys Leu Thr Val Asp Lys Ser Arg Trp Gln Gln Gly Asn
            260                 265                 270

Val Phe Ser Cys Ser Val Met His Glu Ala Leu His Asn His Tyr Thr
        275                 280                 285

Gln Lys Ser Leu Ser Leu Ser Pro Gly Lys Gly Pro Glu Gln Lys Leu
    290                 295                 300

Ile Ser Glu Glu Asp Leu Asn Ser Ala Val Asp His His His His His
305                 310                 315                 320
```

His

<210> SEQ ID NO 5
<211> LENGTH: 81
<212> TYPE: DNA
<213> ORGANISM: Artificial sequence
<220> FEATURE:
<223> OTHER INFORMATION: mCCR5 N' coding polynucleotide

<400> SEQUENCE: 5
atggattttc aagggtcagt tccgacctat agctatgaca tcgattatgg tatgtcagca    60
ccctgccaaa aatcaatgt g                                              81

<210> SEQ ID NO 6
<211> LENGTH: 27
<212> TYPE: PRT
<213> ORGANISM: Artificial sequence
<220> FEATURE:
<223> OTHER INFORMATION: mCCR5 N' polypeptide

<400> SEQUENCE: 6

Met Asp Phe Gln Gly Ser Val Pro Thr Tyr Ser Tyr Asp Ile Asp Tyr
1               5                   10                  15

Gly Met Ser Ala Pro Cys Gln Lys Ile Asn Val
            20                  25

<210> SEQ ID NO 7
<211> LENGTH: 66
<212> TYPE: DNA
<213> ORGANISM: Artificial sequence
<220> FEATURE:
<223> OTHER INFORMATION: mCCR5 EC1 domain coding polynucleotide

<400> SEQUENCE: 7
tatgctgcaa atgagtgggt ctttgggaac ataatgtgta agtattcac agggctctat    60 cacatt                                                              66

<210> SEQ ID NO 8
<211> LENGTH: 22
<212> TYPE: PRT
<213> ORGANISM: Artificial sequence
<220> FEATURE:
<223> OTHER INFORMATION: mCCR5 EC1 domain polypeptide

<400> SEQUENCE: 8

Tyr Ala Ala Asn Glu Trp Val Phe Gly Asn Ile Met Cys Lys Val Phe
1               5                   10                  15

Thr Gly Leu Tyr His Ile
            20

<210> SEQ ID NO 9
<211> LENGTH: 90
<212> TYPE: DNA
<213> ORGANISM: Artificial sequence
<220> FEATURE:
<223> OTHER INFORMATION: mCCR5 EC2 domain coding polynucleotide

<400> SEQUENCE: 9
agatctcaga aagaaggttt tcattataca tgcagtcctc attttccaca cactcagtat    60
catttctgga gagtttcca aacattaaag                                     90

<210> SEQ ID NO 10
<211> LENGTH: 30

```
<212> TYPE: PRT
<213> ORGANISM: Artificial sequence
<220> FEATURE:
<223> OTHER INFORMATION: mCCR5 EC2 domain polypeptide

<400> SEQUENCE: 10

Arg Ser Gln Lys Glu Gly Phe His Tyr Thr Cys Ser Pro His Phe Pro
1               5                   10                  15

His Thr Gln Tyr His Phe Trp Lys Ser Phe Gln Thr Leu Lys
            20                  25                  30

<210> SEQ ID NO 11
<211> LENGTH: 75
<212> TYPE: DNA
<213> ORGANISM: Artificial sequence
<220> FEATURE:
<223> OTHER INFORMATION: mCCR5 EC3 domain coding polynucleotide

<400> SEQUENCE: 11
gaattctttg gactgaataa ctgcagtagt tctaatagac tagaccaggc catgcaggca      60
acagagactc ttgga                                                      75

<210> SEQ ID NO 12
<211> LENGTH: 25
<212> TYPE: PRT
<213> ORGANISM: Artificial sequence
<220> FEATURE:
<223> OTHER INFORMATION: mCCR5 EC3 domain polypeptide

<400> SEQUENCE: 12

Glu Phe Phe Gly Leu Asn Asn Cys Ser Ser Ser Asn Arg Leu Asp Gln
1               5                   10                  15

Ala Met Gln Ala Thr Glu Thr Leu Gly
            20                  25

<210> SEQ ID NO 13
<211> LENGTH: 102
<212> TYPE: DNA
<213> ORGANISM: Artificial sequence
<220> FEATURE:
<223> OTHER INFORMATION: hCCR5 N' coding polynucleotide

<400> SEQUENCE: 13
atggattatc aagtgtcaag tccaatctat gacatcaatt attatacatc ggagccctgc      60
caaaaaatca atgtgaagca atcgcagcc cgcctcctgc ct                         102

<210> SEQ ID NO 14
<211> LENGTH: 34
<212> TYPE: PRT
<213> ORGANISM: Artificial sequence
<220> FEATURE:
<223> OTHER INFORMATION: hCCR5 N' polypeptide

<400> SEQUENCE: 14

Met Asp Tyr Gln Val Ser Ser Pro Ile Tyr Asp Ile Asn Tyr Tyr Thr
1               5                   10                  15

Ser Glu Pro Cys Gln Lys Ile Asn Val Lys Gln Ile Ala Ala Arg Leu
            20                  25                  30

Leu Pro

<210> SEQ ID NO 15
<211> LENGTH: 45
<212> TYPE: DNA
<213> ORGANISM: Artificial sequence
```

```
<220> FEATURE:
<223> OTHER INFORMATION: hCCR5 EC1 domain coding polynucleotide

<400> SEQUENCE: 15
cactatgctg ccgcccagtg ggactttgga aatacaatgt gtcaa                45

<210> SEQ ID NO 16
<211> LENGTH: 15
<212> TYPE: PRT
<213> ORGANISM: Artificial sequence
<220> FEATURE:
<223> OTHER INFORMATION: hCCR5 EC1 domain polypeptide

<400> SEQUENCE: 16

His Tyr Ala Ala Ala Gln Trp Asp Phe Gly Asn Thr Met Cys Gln
1               5                   10                  15

<210> SEQ ID NO 17
<211> LENGTH: 93
<212> TYPE: DNA
<213> ORGANISM: Artificial sequence
<220> FEATURE:
<223> OTHER INFORMATION: hCCR5 EC2 domain coding polynucleotide

<400> SEQUENCE: 17
atctttacca gatctcaaaa agaaggtctt cattacacct gcagctctca ttttccatac      60
agtcagtatc aattctggaa gaatttccag aca                                  93

<210> SEQ ID NO 18
<211> LENGTH: 31
<212> TYPE: PRT
<213> ORGANISM: Artificial sequence
<220> FEATURE:
<223> OTHER INFORMATION: hCCR5 EC2 domain polypeptide

<400> SEQUENCE: 18

Ile Phe Thr Arg Ser Gln Lys Glu Gly Leu His Tyr Thr Cys Ser Ser
1               5                   10                  15

His Phe Pro Tyr Ser Gln Tyr Gln Phe Trp Lys Asn Phe Gln Thr
            20                  25                  30

<210> SEQ ID NO 19
<211> LENGTH: 63
<212> TYPE: DNA
<213> ORGANISM: Artificial sequence
<220> FEATURE:
<223> OTHER INFORMATION: hCCR5 EC3 domain coding polynucleotide

<400> SEQUENCE: 19
caggaattct ttggcctgaa taattgcagt agctctaaca ggttggacca agctatgcag      60
gtg                                                                   63

<210> SEQ ID NO 20
<211> LENGTH: 31
<212> TYPE: PRT
<213> ORGANISM: Artificial sequence
<220> FEATURE:
<223> OTHER INFORMATION: hCCR5 EC3 domain polypeptide

<400> SEQUENCE: 20

Gln Glu Phe Phe Gly Leu Asn Asn Cys Ser Ser Ser Asn Arg Leu Asp
1               5                   10                  15

Gln Ala Met Gln Val Thr Glu Thr Leu Gly Met Thr His Cys Cys
            20                  25                  30
```

<210> SEQ ID NO 21
<211> LENGTH: 693
<212> TYPE: DNA
<213> ORGANISM: Homo sapiens

<400> SEQUENCE: 21

```
cccaaatctt gtgacaaaac tcacacatgc ccaccgtgcc cagcacctga actcctgggg      60
ggaccgtcag tcttcctctt ccccccaaaa cccaaggaca ccctcatgat ctcccggacc     120
cctgaggtca catgcgtggt ggtggacgtg agccacgaag accctgaggt caagttcaac     180
tggtacgtgg acggcgtgga ggtgcataat gccaagacaa agccgcggga ggagcagtac     240
aacagcacgt accgtgtggt cagcgtcctc accgtcctgc accaggactg gctgaatggc     300
aaggagtaca agtgcaaggt ctccaacaaa gccctcccag cccccatcga gaaaaccatc     360
tccaaagcca agggcagccc cgagaaccag gtgtacacc ctgcccccc atcccgggag       420
gagatgacca gaaccaggt cagcctgacc tgcctggtca aaggcttcta tcccagcgac      480
atcgccgtgg agtgggagag caatgggcag ccggagaaca actacaagac cacgcctccc     540
gtgctggact ccgacggctc cttcttcctc tatagcaagc tcaccgtgga caagagcagg     600
tggcagcagg ggaacgtctt ctcatgctcc gtgatgcatg aggctctgca caaccactac     660
acgcagaaga gcctctccct gtccccgggt aaa                                  693
```

<210> SEQ ID NO 22
<211> LENGTH: 231
<212> TYPE: PRT
<213> ORGANISM: Homo sapiens

<400> SEQUENCE: 22

```
Pro Lys Ser Cys Asp Lys Thr His Thr Cys Pro Pro Cys Pro Ala Pro
1               5                  10                  15

Glu Leu Leu Gly Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Glu Met Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
```

```
                     210                 215                 220
Leu Ser Leu Ser Pro Gly Lys
225                 230

<210> SEQ ID NO 23
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 23
ccgctcgagc ccaaatcttg tgacaaaac                                            29

<210> SEQ ID NO 24
<211> LENGTH: 32
<212> TYPE: DNA
<213> ORGANISM: Artificial sequence
<220> FEATURE:
<223> OTHER INFORMATION: Single strand DNA oligonucleotide

<400> SEQUENCE: 24
ttgttcgggc cctttacccg gggacaggga ga                                        32

<210> SEQ ID NO 25
<211> LENGTH: 681
<212> TYPE: DNA
<213> ORGANISM: Mus musculus

<400> SEQUENCE: 25
gtgcccaggg attgtggttg taagccttgc atatgtacag tcccagaagt atcatctgtc          60
ttcatcttcc ccccaaagcc caaggatgtg ctcaccatta ctctgactcc taaggtcacg         120
tgtgttgtgg tagacatcag caaggatgat cccgaggtcc agttcagctg gtttgtagat         180
gatgtggagg tgcacacagc tcagacgcaa ccccgggagg agcagttcaa cagcactttc         240
cgctcagtca gtgaacttcc catcatgcac caggactgcc tcaatggcaa ggagttcaaa         300
tgcagggtca acagtgcagc tttccctgcc cccatcgaga aaaccatctc aaaaccaaa          360 ggcagaccga aggctccaca ggtgtacacc attccacctc ccaaggagca gatggccaag         420
gataaagtca gtctgacctg catgataaca gacttcttcc ctgaagacat tactgtggag         480
tggcagtgga atgggcagcc agcggagaac tacaagaaca ctcagcccat catggacaca         540
gatggctctt acttcgtcta cagcaagctc aatgtgcaga gagcaactg ggaggcagga         600 aatactttca cctgctctgt gttacatgag ggcctgcaca ccaccatac tgagaagagc         660 ctctccccact ctcctggtaa a                                                  681

<210> SEQ ID NO 26
<211> LENGTH: 227
<212> TYPE: PRT
<213> ORGANISM: Mus musculus

<400> SEQUENCE: 26

Val Pro Arg Asp Cys Gly Cys Lys Pro Cys Ile Cys Thr Val Pro Glu
1               5                   10                  15

Val Ser Ser Val Phe Ile Phe Pro Pro Lys Pro Lys Asp Val Leu Thr
            20                  25                  30

Ile Thr Leu Thr Pro Lys Val Thr Cys Val Val Val Asp Ile Ser Lys
        35                  40                  45

Asp Asp Pro Glu Val Gln Phe Ser Trp Phe Val Asp Asp Val Glu Val
    50                  55                  60
```

```
His Thr Ala Gln Thr Gln Pro Arg Glu Glu Gln Phe Asn Ser Thr Phe
 65                  70                  75                  80

Arg Ser Val Ser Glu Leu Pro Ile Met His Gln Asp Cys Leu Asn Gly
             85                  90                  95

Lys Glu Phe Lys Cys Arg Val Asn Ser Ala Ala Phe Pro Ala Pro Ile
        100                 105                 110

Glu Lys Thr Ile Ser Lys Thr Lys Gly Arg Pro Lys Ala Pro Gln Val
    115                 120                 125

Tyr Thr Ile Pro Pro Lys Glu Gln Met Ala Lys Asp Lys Val Ser
130                 135                 140

Leu Thr Cys Met Ile Thr Asp Phe Phe Pro Glu Asp Ile Thr Val Glu
145                 150                 155                 160

Trp Gln Trp Asn Gly Gln Pro Ala Glu Asn Tyr Lys Asn Thr Gln Pro
                165                 170                 175

Ile Met Asp Thr Asp Gly Ser Tyr Phe Val Tyr Ser Lys Leu Asn Val
                180                 185                 190

Gln Lys Ser Asn Trp Glu Ala Gly Asn Thr Phe Thr Cys Ser Val Leu
            195                 200                 205

His Glu Gly Leu His Asn His His Thr Glu Lys Ser Leu Ser His Ser
    210                 215                 220

Pro Gly Lys
225

<210> SEQ ID NO 27
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 27
ccgctcgagg tgcccaggga ttgtggttg                                    29

<210> SEQ ID NO 28
<211> LENGTH: 32
<212> TYPE: DNA
<213> ORGANISM: Artificial sequence
<220> FEATURE:
<223> OTHER INFORMATION: Single strand DNA oligonucleotide

<400> SEQUENCE: 28
ttgttcgggc cctttaccag gagagtggga ga                                32

<210> SEQ ID NO 29
<211> LENGTH: 1065
<212> TYPE: DNA
<213> ORGANISM: Mus musculus

<400> SEQUENCE: 29
atggattttc aagggtcagt tccgacctat agctatgaca tcgattatgg tatgtcagca    60
ccctgccaaa aaatcaatgt gaaacaaatt gcggctcagc tcctgccccc actctactcc   120
ctggtattca tctttggttt tgtgggtaac atgatggtct tcctcatctt gataagctgc   180
aaaaagctga gagcgtgac tgatatctac ctgctcaacc tggccatctc tgacctgctc   240
ttcctgctca cactaccatt ctgggctcac tatgctgcaa atgagtgggt ctttgggaac   300
ataatgtgta agtattcac agggctctat acattggtt attttggtgg aatcttcttc   360
attatcctcc tgacaattga taggtacttg gctattgtcc atgctgtgtt tgctttaaaa   420
```

```
gtcagaacgg tcaactttgg ggtgataaca agtgtagtca cttgggcggt ggctgtgttt    480
gcctctctcc cagaaataat ctttaccaga tctcagaaag aaggttttca ttatacatgc    540
agtcctcatt ttccacacac tcagtatcat ttctggaaga gtttccaaac attaaagatg    600
gtcatcttga gcctgatcct gcctctactt gtcatggtca tctgctactc aggaattctc    660
cacaccctgt ttcgctgtag gaatgagaag aagaggcaca gggctgtgag gctcatcttt    720
gccatcatga ttgtctactt tctcttctgg actccctaca acattgtcct cctcctgacc    780
accttccagg aattctttgg actgaataac tgcagtagtt ctaatagact agaccaggcc    840
atgcaggcaa cagagactct tggaatgaca cactgctgcc taaaccctgt catctatgcc    900
tttgttggag agaagttccg gagttatctc tcagtgttct tccgaaaaca catggtcaaa    960
cgcttttgca acggtgttc aatttttccag caagacaatc ctgatcgtgc aagctcagtc   1020 tataccccgat ccacaggaga acatgaagtt tctactggtt tatga                   1065
```

<210> SEQ ID NO 30
<211> LENGTH: 354
<212> TYPE: PRT
<213> ORGANISM: Mus musculus

<400> SEQUENCE: 30

```
Met Asp Phe Gln Gly Ser Val Pro Thr Tyr Ser Tyr Asp Ile Asp Tyr
1               5                   10                  15

Gly Met Ser Ala Pro Cys Gln Lys Ile Asn Val Lys Gln Ile Ala Ala
            20                  25                  30

Gln Leu Leu Pro Pro Leu Tyr Ser Leu Val Phe Ile Phe Gly Phe Val
        35                  40                  45

Gly Asn Met Met Val Phe Leu Ile Leu Ile Ser Cys Lys Lys Leu Lys
    50                  55                  60

Ser Val Thr Asp Ile Tyr Leu Leu Asn Leu Ala Ile Ser Asp Leu Leu
65                  70                  75                  80

Phe Leu Leu Thr Leu Pro Phe Trp Ala His Tyr Ala Ala Asn Glu Trp
                85                  90                  95

Val Phe Gly Asn Ile Met Cys Lys Val Phe Thr Gly Leu Tyr His Ile
            100                 105                 110

Gly Tyr Phe Gly Gly Ile Phe Phe Ile Ile Leu Leu Thr Ile Asp Arg
        115                 120                 125

Tyr Leu Ala Ile Val His Ala Val Phe Ala Leu Lys Val Arg Thr Val
    130                 135                 140

Asn Phe Gly Val Ile Thr Ser Val Val Thr Trp Ala Val Ala Val Phe
145                 150                 155                 160

Ala Ser Leu Pro Glu Ile Ile Phe Thr Arg Ser Gln Lys Glu Gly Phe
                165                 170                 175

His Tyr Thr Cys Ser Pro His Phe Pro His Thr Gln Tyr His Phe Trp
            180                 185                 190

Lys Ser Phe Gln Thr Leu Lys Met Val Ile Leu Ser Leu Ile Leu Pro
        195                 200                 205

Leu Leu Val Met Val Ile Cys Tyr Ser Gly Ile Leu His Thr Leu Phe
    210                 215                 220

Arg Cys Arg Asn Glu Lys Lys Arg His Arg Ala Val Arg Leu Ile Phe
225                 230                 235                 240

Ala Ile Met Ile Val Tyr Phe Leu Phe Trp Thr Pro Tyr Asn Ile Val
                245                 250                 255

Leu Leu Leu Thr Thr Phe Gln Glu Phe Phe Gly Leu Asn Asn Cys Ser
            260                 265                 270
```

```
Ser Ser Asn Arg Leu Asp Gln Ala Met Gln Ala Thr Glu Thr Leu Gly
        275                 280                 285

Met Thr His Cys Cys Leu Asn Pro Val Ile Tyr Ala Phe Val Gly Glu
    290                 295                 300

Lys Phe Arg Ser Tyr Leu Ser Val Phe Phe Arg Lys His Met Val Lys
305                 310                 315                 320

Arg Phe Cys Lys Arg Cys Ser Ile Phe Gln Gln Asp Asn Pro Asp Arg
                325                 330                 335

Ala Ser Ser Val Tyr Thr Arg Ser Thr Gly Glu His Glu Val Ser Thr
            340                 345                 350

Gly Leu

<210> SEQ ID NO 31
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 31
cccaagctta gatctcagaa agaaggttt                                    29

<210> SEQ ID NO 32
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 32
ccgctcgagc tttaatgttt ggaaactct                                    29

<210> SEQ ID NO 33
<211> LENGTH: 1059
<212> TYPE: DNA
<213> ORGANISM: Homo sapiens

<400> SEQUENCE: 33
atggattatc aagtgtcaag tccaatctat gacatcaatt attatacatc ggagccctgc    60
caaaaaatca atgtgaagca aatcgcagcc cgcctcctgc ctccgctcta ctcactggtg   120
ttcatctttg gttttgtggg caacatgctg gtcatcctca tcctgataaa ctgcaaaagg   180
ctgaagagca tgactgacat ctacctgctc aacctggcca tctctgacct gttttctt   240 cttactgtcc ccttctgggc tcactatgct gccgcccagt gggactttgg aaatacaatg   300
tgtcaactct tgacagggct ctattttata ggcttcttct ctggaatctt cttcatcatc   360
ctcctgacaa tcgataggta cctggctgtc gtccatgctg tgtttgcttt aaaagccagg   420 acggtcaccct ttggggtggt gacaagtgtg atcacttggg tggtggctgt gtttgcgtct   480
ctcccaggaa tcatctttac cagatctcaa aaagaaggtc ttcattacac ctgcagctct   540 catttttccat acagtcagta tcaattctgg aagaatttcc agacattaaa gatagtcatc   600
ttggggctgg tcctgccgct gcttgtcatg gtcatctgct actcgggaat cctaaaaact   660
ctgcttcggt gtcgaaatga aagaagagg cacagggctg tgaggcttat cttcaccatc   720
atgattgttt atttctctt ctgggctccc tacaacattg tccttctcct gaacaccttc   780
caggaattct ttggcctgaa taattgcagt agctctaaca ggttggacca agctatgcag   840
gtgacagaga ctcttgggat gacgcactgc tgcatcaacc ccatcatcta tgcctttgtc   900
```

-continued

```
ggggagaagt tcagaaacta cctcttagtc ttcttccaaa agcacattgc caaacgcttc    960
tgcaaatgct gttctatttt ccagcaagag gctcccgagc gagcaagctc agtttacacc   1020
cgatccactg gggagcagga aatatctgtg ggcttgtga                          1059
```

<210> SEQ ID NO 34
<211> LENGTH: 352
<212> TYPE: PRT
<213> ORGANISM: Homo sapiens

<400> SEQUENCE: 34

```
Met Asp Tyr Gln Val Ser Ser Pro Ile Tyr Asp Ile Asn Tyr Tyr Thr
1               5                   10                  15

Ser Glu Pro Cys Gln Lys Ile Asn Val Lys Gln Ile Ala Ala Arg Leu
            20                  25                  30

Leu Pro Pro Leu Tyr Ser Leu Val Phe Ile Phe Gly Phe Val Gly Asn
        35                  40                  45

Met Leu Val Ile Leu Ile Leu Ile Asn Cys Lys Arg Leu Lys Ser Met
    50                  55                  60

Thr Asp Ile Tyr Leu Leu Asn Leu Ala Ile Ser Asp Leu Phe Phe Leu
65                  70                  75                  80

Leu Thr Val Pro Phe Trp Ala His Tyr Ala Ala Ala Gln Trp Asp Phe
                85                  90                  95

Gly Asn Thr Met Cys Gln Leu Leu Thr Gly Leu Tyr Phe Ile Gly Phe
            100                 105                 110

Phe Ser Gly Ile Phe Phe Ile Ile Leu Leu Thr Ile Asp Arg Tyr Leu
        115                 120                 125

Ala Val Val His Ala Val Phe Ala Leu Lys Ala Arg Thr Val Thr Phe
    130                 135                 140

Gly Val Val Thr Ser Val Ile Thr Trp Val Val Ala Val Phe Ala Ser
145                 150                 155                 160

Leu Pro Gly Ile Ile Phe Thr Arg Ser Gln Lys Glu Gly Leu His Tyr
                165                 170                 175

Thr Cys Ser Ser His Phe Pro Tyr Ser Gln Tyr Gln Phe Trp Lys Asn
            180                 185                 190

Phe Gln Thr Leu Lys Ile Val Ile Leu Gly Leu Val Leu Pro Leu Leu
        195                 200                 205

Val Met Val Ile Cys Tyr Ser Gly Ile Leu Lys Thr Leu Leu Arg Cys
    210                 215                 220

Arg Asn Glu Lys Lys Arg His Arg Ala Val Arg Leu Ile Phe Thr Ile
225                 230                 235                 240

Met Ile Val Tyr Phe Leu Phe Trp Ala Pro Tyr Asn Ile Val Leu Leu
                245                 250                 255

Leu Asn Thr Phe Gln Glu Phe Phe Gly Leu Asn Asn Cys Ser Ser Ser
            260                 265                 270

Asn Arg Leu Asp Gln Ala Met Gln Val Thr Glu Thr Leu Gly Met Thr
        275                 280                 285

His Cys Cys Ile Asn Pro Ile Ile Tyr Ala Phe Val Gly Glu Lys Phe
    290                 295                 300

Arg Asn Tyr Leu Leu Val Phe Phe Gln Lys His Ile Ala Lys Arg Phe
305                 310                 315                 320

Cys Lys Cys Cys Ser Ile Phe Gln Gln Glu Ala Pro Glu Arg Ala Ser
                325                 330                 335

Ser Val Tyr Thr Arg Ser Thr Gly Glu Gln Glu Ile Ser Val Gly Leu
            340                 345                 350
```

```
<210> SEQ ID NO 35
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 35
cccaagctta ccagatctca aaaagaagg                                          29

<210> SEQ ID NO 36
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 36
ccgctcgaga ttcttccaga attgatact                                          29

<210> SEQ ID NO 37
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 37
cccaagctta tggattttca agggtcagt                                          29

<210> SEQ ID NO 38
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 38
ccgctcgagc acattgattt tttggcagg                                          29

<210> SEQ ID NO 39
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 39
cccaagcttt atgctgcaaa tgagtgggt                                          29

<210> SEQ ID NO 40
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 40
ccgctcgaga atgtgataga gccctgtga                                          29

<210> SEQ ID NO 41
<211> LENGTH: 29
<212> TYPE: DNA
<213> ORGANISM: Artificial sequence
<220> FEATURE:
<223> OTHER INFORMATION: Single strand DNA oligonucleotide
```

```
<400> SEQUENCE: 41
cccaagcttg aattctttgg actgaataa                                29

<210> SEQ ID NO 42
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 42
ccgctcgagc attccaagag tctctgttg                                29
```

MOLECULES AND METHODS OF USING SAME FOR TREATING CCR5/CCR5 LIGANDS ASSOCIATED DISEASES

RELATED APPLICATIONS

This Application is a National Phase of PCT Patent Application No. PCT/IL2007/000219 having International filing date of Feb. 18, 2007, which claims the benefit of U.S. Provisional Patent Application Nos. 60/789,920 filed on Apr. 7, 2006; 60/774,191 filed on Feb. 17, 2006 The contents of the above Applications are all incorporated herein by reference.

FIELD AND BACKGROUND OF THE INVENTION

The present invention relates to novel molecules and, more particularly, to methods of treating CCR5/CCR5-ligands associated diseases, such as autoimmune inflammatory diseases.

Chemokines are small (~8-14 kDa), structurally cytokine-like, secreted proteins that regulate cell trafficking. They are produced and secreted by a wide variety of cell types in response to early inflammatory mediators, such as IL-1β or TNF-α, and in response to bacterial or viral infection. Chemokines function mainly as chemoattractants for leukocytes, recruiting monocytes, neutrophils and other effector cells from the blood to sites of infection or damage. They can be released by many different cell types (e.g. macrophages) and can mediate a range of pro-inflammatory effects on leukocytes, such as triggering of chemotaxis, degranulation, synthesis of lipid mediators, and integrin activation.

Chemokines can be subdivided into four classes, the C—C, C—X—C, C and C—X3-C chemokines, depending on the location of the first two cysteines in their protein sequence. The interaction of these soluble proteins with their specific receptors, which belong to the superfamily of seven-transmembrane domain G-protein-coupled receptors (GPCRs), mediate their biological effects resulting in, among other responses, rapid increase in intracellular calcium concentration, changes in cell shape, increased expression of cellular adhesion molecules, degranulation, and promotion of cell migration.

In the last several years, the key role of chemokines as important mediators in inflammatory and autoimmune disorders and diseases has been well established. Chemokines have been indicated as important mediators in multiple sclerosis (MS), allergic responses, asthma, atherosclerosis, glomerulonephritis, pancreatitis, restenosis, rheumatoid arthritis (RA), diabetic nephropathy, pulmonary fibrosis, transplant rejection and in cancer.

Among the most prominent chemokines mentioned in disorders and diseases are the C—C chemokines: MIP-1α (Macrophage inflammatory protein 1α, CCL3) and RANTES (Regulated upon Activation, Normal T-cell Expressed, and Secreted, CCL5). MIP-1α is produced by macrophages and is an activator of human granulocytes (neutrophils, eosinophils and basophils). MIP-1α induces the synthesis and release of pro-inflammatory cytokines such as interleukin 1 (IL-1), IL-6 and TNF-α from fibroblasts and macrophages. RANTES is secreted by peripheral blood mononuclear cells (PBMC) and is a chemotactic factor for T cells, eosinophils and basophils. RANTES plays an active role in recruiting leukocytes into inflammatory sites and in inducing proliferation and activation of certain natural killer (NK) cells.

The C—C Chemokine Receptor 5 (CCR5) is expressed on several cell types including peripheral blood-derived dendritic cells, CD34+ hematopoietic progenitor cells and certain activated/memory Th1 lymphocytes. CCR5 has several C—C chemokine ligands which include CCL2 (MCP-1), CCL3 (MIP-1α), CCL4 (MIP-113), CCL5 (RANTES), CCL11 (eotaxin) and CCL16 [Blanpain et al., Blood. (1999) 94:1899-905; Nomiyama et al., Int Immunol (2001) (8):1021-9], most of which play a central role in pathogenesis.

Thus, recent studies have demonstrated the significance of CCR5 receptor and ligands in inflammatory diseases such as Rheumatoid Arthritis (RA) and Multiple Sclerosis (MS). In RA, the specific expression of CCR5 has been demonstrated on macrophages and on most T lymphocytes in the rheumatoid synovial fluid and membrane [Pokorny et al., Ann Rheum Dis (2005) 64:487-490; Wang and Liu, Clin Exp Immunol (2003) 132:371-8; Nissinen et al., J Rheumatol (2003) 30:1928-34; Mack et al., Arthritis Rheum (1999) 42:981-8] while elevated levels of chemokines, including MIP-1α (CCL3) and RANTES (CCL5), have been shown in RA synovial fluids [Hayashida et al., Arthritis Res (2001) 3(2):118-126; Loetscher and Moser, Arthritis Res (2002) 4(4):233-236]. MS is characterized by infiltration of inflammatory cells (predominantly CD4+Th1 cells) into the central nervous system (CNS). Inflammatory T cells have been shown to migrate towards RANTES and MIP-1α as a result of over expression of their receptors (CCR5) on these cells [Zang et al., Brain (2000) 123(9):1874-1882].

Thus, the potential therapeutic value of antagonizing the CCR5/ligand axis has been demonstrated.

Various approaches for blocking CCR5 activation have been attempted, some are summarized infra.

PCT Publication No. WO05078097 discloses a multifunctional short interfering nucleic acid (multifunctional siNA) molecule that modulates the expression of genes, such as CCR5, via RNA interference (RNAi) and could potentially be useful in the treatment of any disease or condition that responds to modulation of gene expression or activity. Although RNAi are known to be highly sequence specific, the decreasing rate of gene expression and protein disappearance depends on the type of targeted cell, the rate of cell division and the protein half-life. In addition, siRNA may not completely inhibit the expression of the protein and some molecules may still be transcribed, therefore, targeting the end product (the protein target itself) rather than the genes would be preferred.

U.S. Pat. No. 6,930,174 discloses CCR5 chemokine receptor-specific monoclonal antibodies which compete for receptor binding therefore blocking natural responses by interfering with ligand-receptor interactions. The contemplated use for these antibodies include treatment and/or prevention of inflammatory diseases, including rheumatoid arthritis, viral infections including Human Immunodeficiency Viruses 1 and 2 (HIV-1 and 2), cancer and auto-immune disorders. This invention has the disadvantages of using mAb: 1) they may induce anti idiotypic responses in the host; 2) they compete for receptor binding yet they do not neutralize the ligands which may still transmit activating signals. Extracellular fragments of the receptor are contemplated for antibody production including N-terminus and the first extracellular loop (EC1). EC2 is not mentioned.

U.S. Pat. No. 20030166870 discloses a mAb which binds specifically to CCR5 (anti-CCR5) and thus inhibits CCR5 functions including CCR5 binding activity (e.g. ligand binding, including RANTES, MIP-1.alpha. and/or MIP-1.beta), signaling activity (e.g., activation of a mammalian G protein) and/or stimulation of a cellular response (e.g., stimulation of chemotaxis). This anti-CCR5 mAb could be used for therapeutic interventions of inflammatory diseases as well as for HIV-1 and 2. This invention has the disadvantages of using mAb as described hereinabove. In addition, the inventors of this application, explicitly state that both the EC2 domain and the amino terminus domain of CCR5 are important for CCR5 ligand binding as manifested by their suggested epitopes for bi-specific antibody production. Receptor chimeras were described which comprise the second extracellular domain of CCR5 yet these chimeras were CCR5/CCR2 chimeras constructed by transferring restriction fragments flanked by the common BamHI, AflII, ClaI, EcoRI, and XbaI sites between human CCR5 and human CCR2b. However, these receptors can only be membrane bound and are not suitable as soluble therapeutic receptors.

To overcome these limitations, a soluble receptor-based approach has been suggested. Basically, a soluble receptor decoy which comprises the ligand binding domain is used to sequester all ligand-mediated receptor activation. The soluble receptor based approach has few apparent advantages over mAb based therapies, first, they do not readily induce anti idiotypic responses in the host, as antibodies do; in addition, according to their nature, they bind the biologically functional determinant of the ligand (which apparently transmits activating signaling in the natural receptor) and are therefore highly effective neutralizing compounds; finally, they present minimal safety issues.

U.S. Pat. No. 6,800,729 discloses a CCR5 variant (also referred to as HDGNR10) that can be used for treating diseases including chronic infections, leukemia and T-cell mediated auto-immune diseases. This invention describes a full size CCR5 protein of 352 amino acid residues with a high degree of homology to a human MCP-1 receptor. A soluble form of the described CCR5 is suggested to bind the physiological ligands (such as MIP-1) and thus may prevent the ligands from interacting with membrane bound CCR5. This invention teaches a full size CCR5 protein which is extremely large and is not compatible with therapy due to low bioavailability and degradation.

PCT Publication No. WO05106489 discloses human CCR5 fusion proteins, which can be used for diagnostics and therapeutics of diseases associated with C—C chemokines, including inflammatory diseases, hematological disorders and cancer. This fusion protein comprises a CCR5 protein fused to a galactosidase portion. This invention also provides methods of screening for therapeutic agents using the CCR5 polypeptide. Thus compounds which bind to CCR5 and inactivate CCR5-mediated signaling are identified as potential therapeutic agents. However, the teachings of this invention do not indicate which domain should be included in the CCR5 fusion. As mentioned, CCR5 is a large protein with a few extracellular domains. Whole soluble extracellular domain is very difficult to construct and is absolutely not compatible with therapy due to its bioavailability and degradation.

There is thus a widely recognized need and it would be highly advantageous to have therapeutic modalities which target CCR5 and its ligands and that can be used in the treatment of a myriad of inflammatory and autoimmune diseases which pathogenicity involves these proteins.

SUMMARY OF THE INVENTION

According to one aspect of the present invention there is provided a soluble molecule comprising a heterologous amino acid sequence conjugated to a CCR5 amino acid sequence being capable of binding a CCR5 ligand, and wherein the molecule is devoid of an N-terminus domain of CCR5.

According to another aspect of the present invention there is provided a soluble molecule comprising a CCR5 amino acid sequence attached to a non-proteinaceous moiety, wherein the CCR5 amino acid sequence is capable of binding a CCR5 ligand and whereas the molecule is non-immunogenic in a subject.

According to yet another aspect of the present invention there is provided a soluble molecule comprising at least two non-contiguous CCR5 amino acid sequences each being capable of binding a CCR5 ligand.

According to still another aspect of the present invention there is provided a molecule comprising a tag attached to a CCR5 amino acid sequence devoid of an N-terminus domain of CCR5, the CCR5 amino acid sequence being capable of binding a CCR5 ligand.

According to an additional aspect of the present invention there is provided a molecule as set forth in SEQ ID NO: 2 or 4.

According to yet an additional aspect of the present invention there is provided an isolated polynucleotide comprising a nucleic acid sequence encoding the molecule.

According to still an additional aspect of the present invention there is provided a pharmaceutical composition comprising as an active ingredient the molecule and a pharmaceutically acceptable carrier.

According to a further aspect of the present invention there is provided a method of treating a CCR5 and/or a CCR5 ligand-associated disease in a subject in need thereof, the method comprising administering to the subject a therapeutically effective amount of the molecule, thereby treating the CCR5 and/or CCR5 ligand associated disease in the subject.

According to yet a further aspect of the present invention there is provided a use of the molecule for the manufacture of a medicament identified for treating CCR5 and/or CCR5 ligand-associated diseases.

According to still a further aspect of the present invention there is provided a method of isolating a CCR5 ligand from a biological sample, the method comprising: (a) contacting the biological sample with the molecule of claim 4 such that the CCR5-ligand and the molecule of claim 4 form a complex; and (b) isolating the complex to thereby isolate the CCR5 ligand from the biological sample.

According to further features in preferred embodiments of the invention described below, wherein the CCR5 ligand is selected from the group consisting of CCL2, CCL3, CCL4, CCL5, CCL11 and CCL16.

According to still further features in the described preferred embodiments wherein the molecule is non-immunogenic.

According to still further features in the described preferred embodiments wherein a binding affinity of the CCR5 to the CCR5 ligand is above $K_D=10^{-6}$ M.

According to still further features in the described preferred embodiments wherein the heterologous amino acid sequence comprises an immunoglobulin amino acid sequence.

According to still further features in the described preferred embodiments wherein the CCR5 amino acid sequence is as set forth in SEQ ID NO: 10 or 18.

According to still further features in the described preferred embodiments wherein the disease is selected from the group consisting of multiple sclerosis, rheumatoid arthritis and type 1 diabetes mellitus.

According to still further features in the described preferred embodiments wherein the tag is an epitope tag.

According to still further features in the described preferred embodiments wherein the molecule is attached to a solid support.

According to still further features in the described preferred embodiments the molecules is attached to a non-protein moiety.

According to still further features in the described preferred embodiments wherein the non-protein moiety is selected from the group consisting of polyethylene glycol (PEG), Polyvinyl pyrrolidone (PVP), poly(styrene comaleic anhydride) (SMA), and divinyl ether and maleic anhydride copolymer (DIVEMA).

According to still further features in the described preferred embodiments wherein the pharmaceutically acceptable carrier is formulated for parenteral administration.

According to still further features in the described preferred embodiments wherein the pharmaceutically acceptable carrier is substantially non-immunogenic.

According to still further features in the described preferred embodiments wherein the pharmaceutically acceptable carrier comprises a lipoamine acid.

According to still further features in the described preferred embodiments wherein the pharmaceutically acceptable carrier comprises a carbohydrate.

According to still further features in the described preferred embodiments wherein the pharmaceutically acceptable carrier comprises a microsphere.

According to still further features in the described preferred embodiments wherein the pharmaceutically acceptable carrier comprises a liposome.

According to still further features in the described preferred embodiments wherein the pharmaceutically acceptable carrier comprises a polymer microsphere.

The present invention successfully addresses the shortcomings of the presently known configurations by providing soluble molecules, compositions and methods of using same for the treatment of CCR5/CCR5-ligand associated diseases.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a schematic illustration depicting the generation of the expression construct encoding the human Ig-CCR5-EC2 peptide of the present invention (SEQ ID NO: 4).

FIGS. 2A-C are bar graphs depicting the binding specificity of EC1, EC2, EC3 and N domains of the murine CCR5-IgG fusion proteins to various commercially available murine recombinant C—C chemokines: MIP-1α (CCL3), MIP-1β (CCL4) and RANTES (CCL5). Specific binding was determined by direct ELISA. Results are shown as O.D. reading at 450 nm. FIG. 2A depicts dose dependent binding of mCCR5 (EC1, EC2, EC3 or N)-IgG to mCCL3. FIG. 2B depicts dose dependent binding of mCCR5 (EC1, EC2, EC3 or N)-IgG to mCCL4. FIG. 2C depicts dose dependent binding of mCCR5 (EC1, EC2, EC3 or N)-IgG to mCCL5.

Figure 3A:
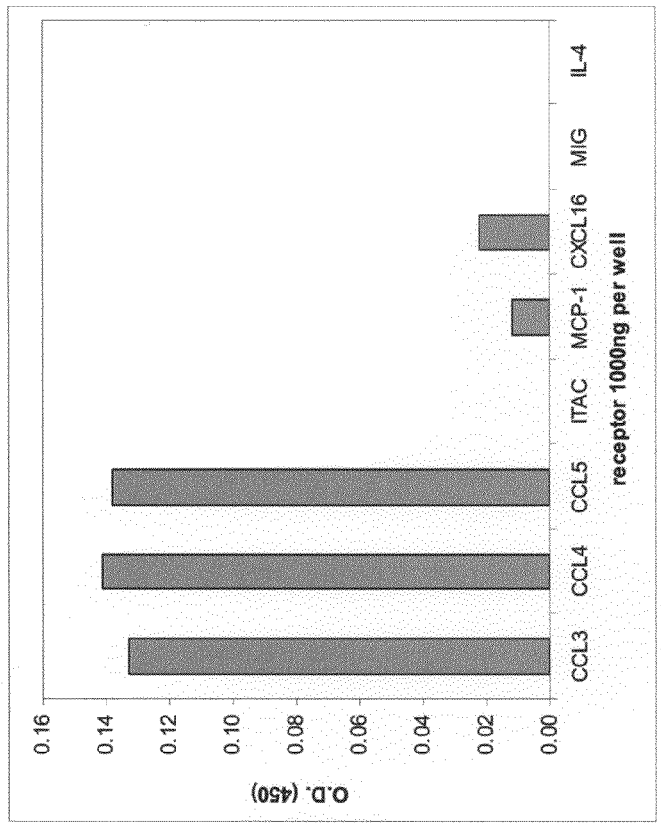
Figure 3B:
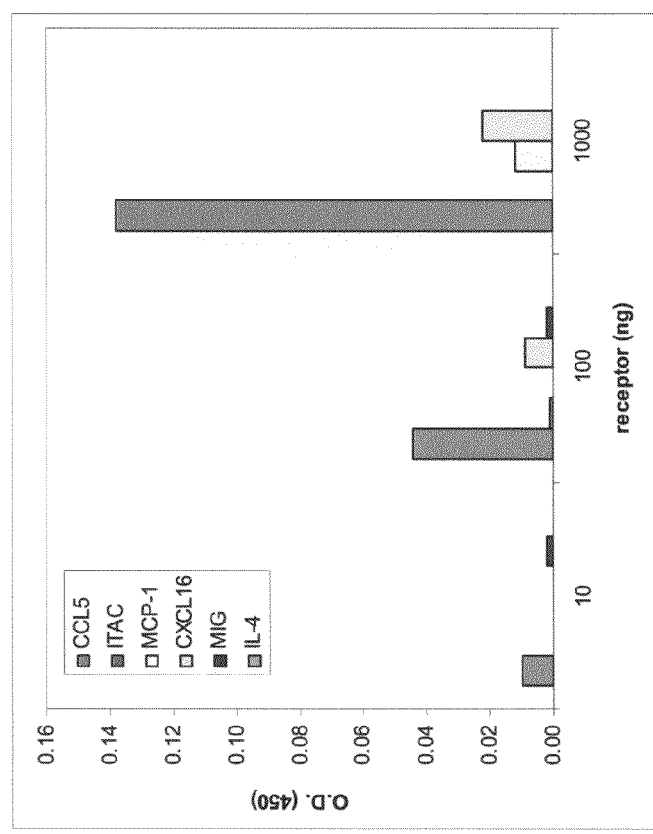

FIGS. 3A-B are bar graphs depicting the ability of the soluble receptor mCCR5(EC2)-IgG to bind different murine chemokines: MIP-1α (CCL3), MIP-1β (CCL4), RANTES (CCL5), ITAC, MCP-1 (CCL2), CXCL16, MIG and IL-4. Specific binding was determined by direct ELISA. Results are shown as O.D. reading at 450 nm. FIG. 2A is a graph showing binding differing concentrations of soluble mCCR5 (EC2)-IgG to the above described cytokines. FIG. 2B is a graph showing the binding of 1000 ng soluble mCCR5(EC2)-IgG to the above described cytokines (single concentration).

Figure 4:
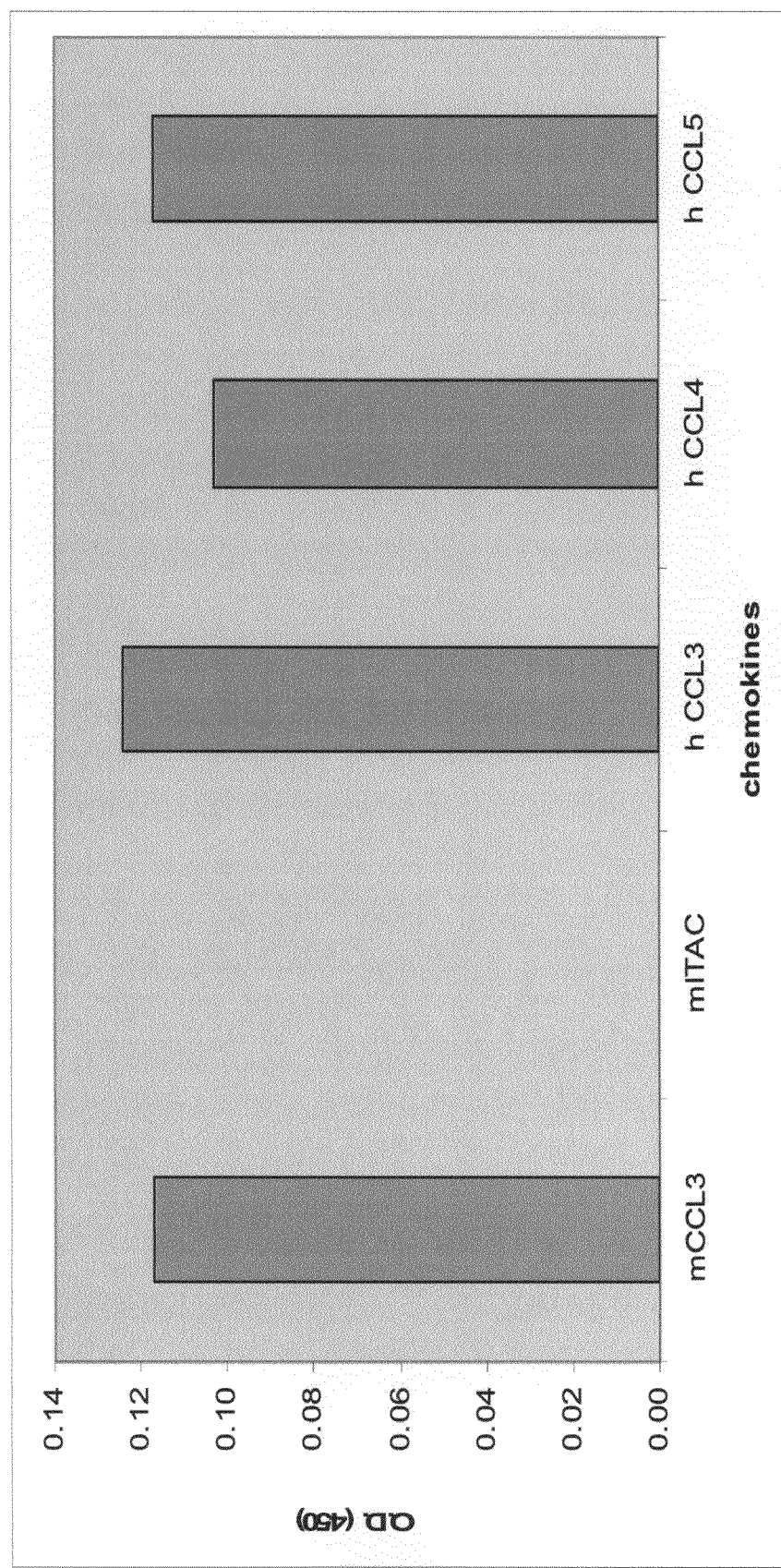

FIG. 4 is a bar graph depicting cross reactivity between mCCR5(EC2)-IgG and human CCL3, CCL4 and CCL5. Murine CCL3 was used as positive control of receptor binding, while mITAC was used as a negative control. Specific binding was determined by direct ELISA. Results are shown as O.D. reading at 450 nm.

Figure 5A:
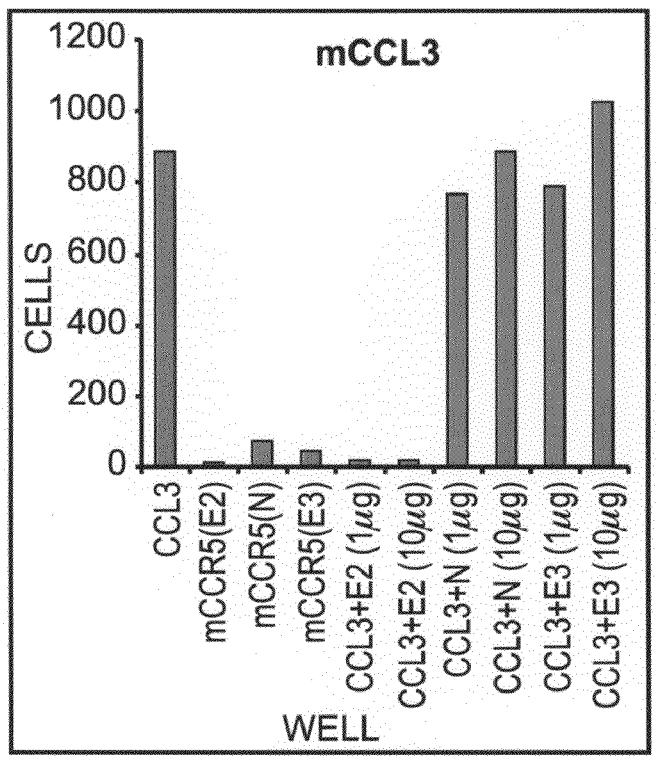
Figure 5B:
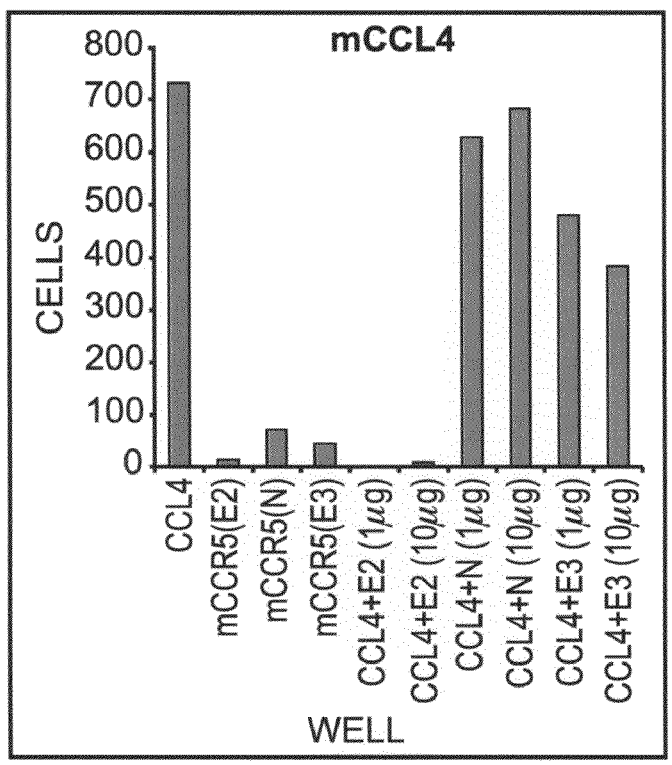
Figure 5C:
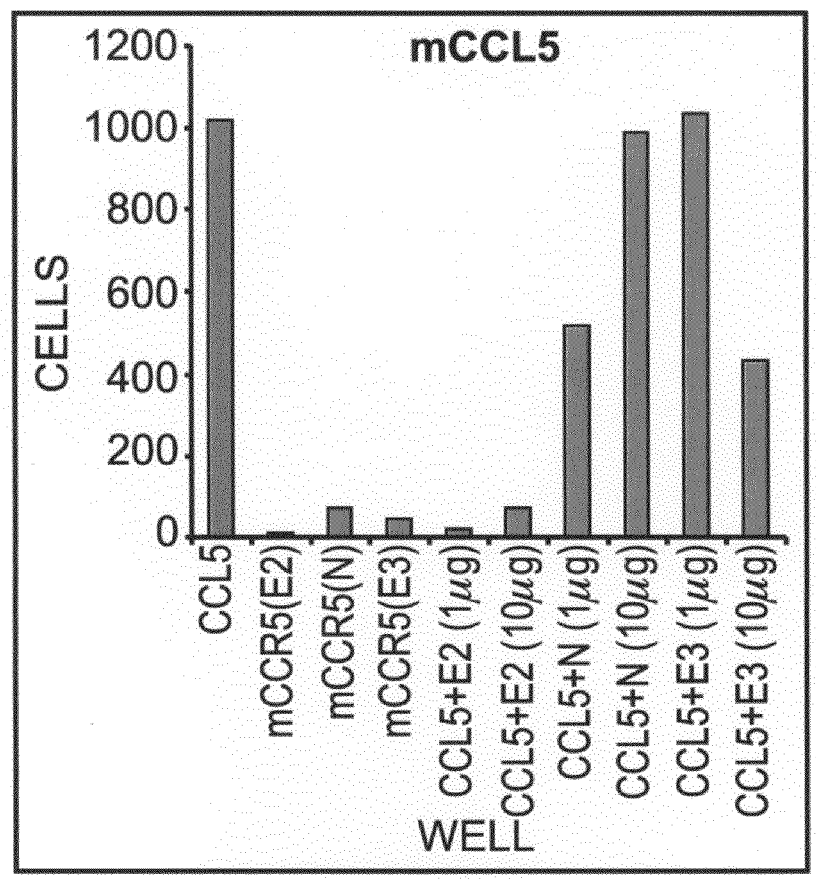

FIGS. 5A-C are bar graphs depicting the ability of EC2, EC3 and N domains of mCCR5-Ig to specifically neutralize CCL3, CCL4 and CCL5 induced THP-1 cell migration. An in vitro transwell migration assay was performed. In brief, transwells were incubated for 30 minutes with 15 ng/well murine CCL3, 10 ng/well murine CCL4 and 50 ng/well murine CCL5 along with 1 μg/well or 10 μg/well of the different mCCR5-IgG extracellular domains (as stated above). THP-1 cells were starved for 24 hours and were added to the upper chamber of the transwell plate. Following 3 hours of incubation at 37° C. migrating THP-1 cells were counted by FACS. FIG. 5A is a graph showing chemotaxis induced by murine CCL3. FIG. 5B is a graph showing chemotaxis induced by murine CCL4. FIG. 5C is a graph showing chemotaxis induced by murine CCL5.

Figure 6:
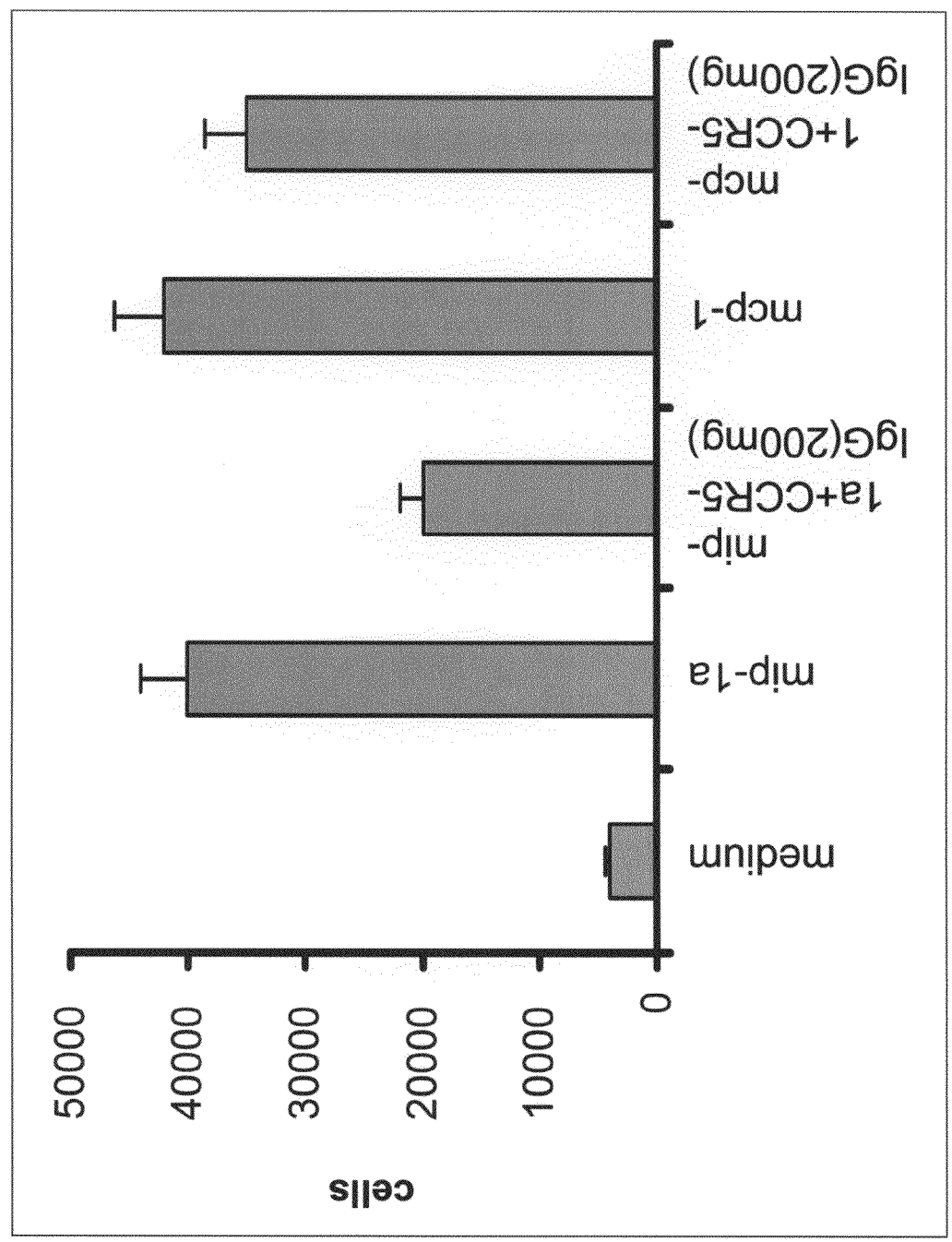

FIG. 6 is a bar graph depicting the ability of human CCR5-IgG to inhibit MIP-1α (CCL3) induced migration of THP-1 cells. An in vitro transwell migration assay was performed. In brief, THP-1 cells ($10^6$/well) were added to the upper chamber of the transwell plate and CCL3 (recombinant human MIP-1α) or the control CCL2 (recombinant human MCP-1) were added to the lower well supplemented with or without hCCR5-IgG as shown in the Figure. Following 3 hours of incubation at 37° C. migrating THP-1 cells were counted by FACS. Result are shown as mean of triplicates±SE.

Figure 7:
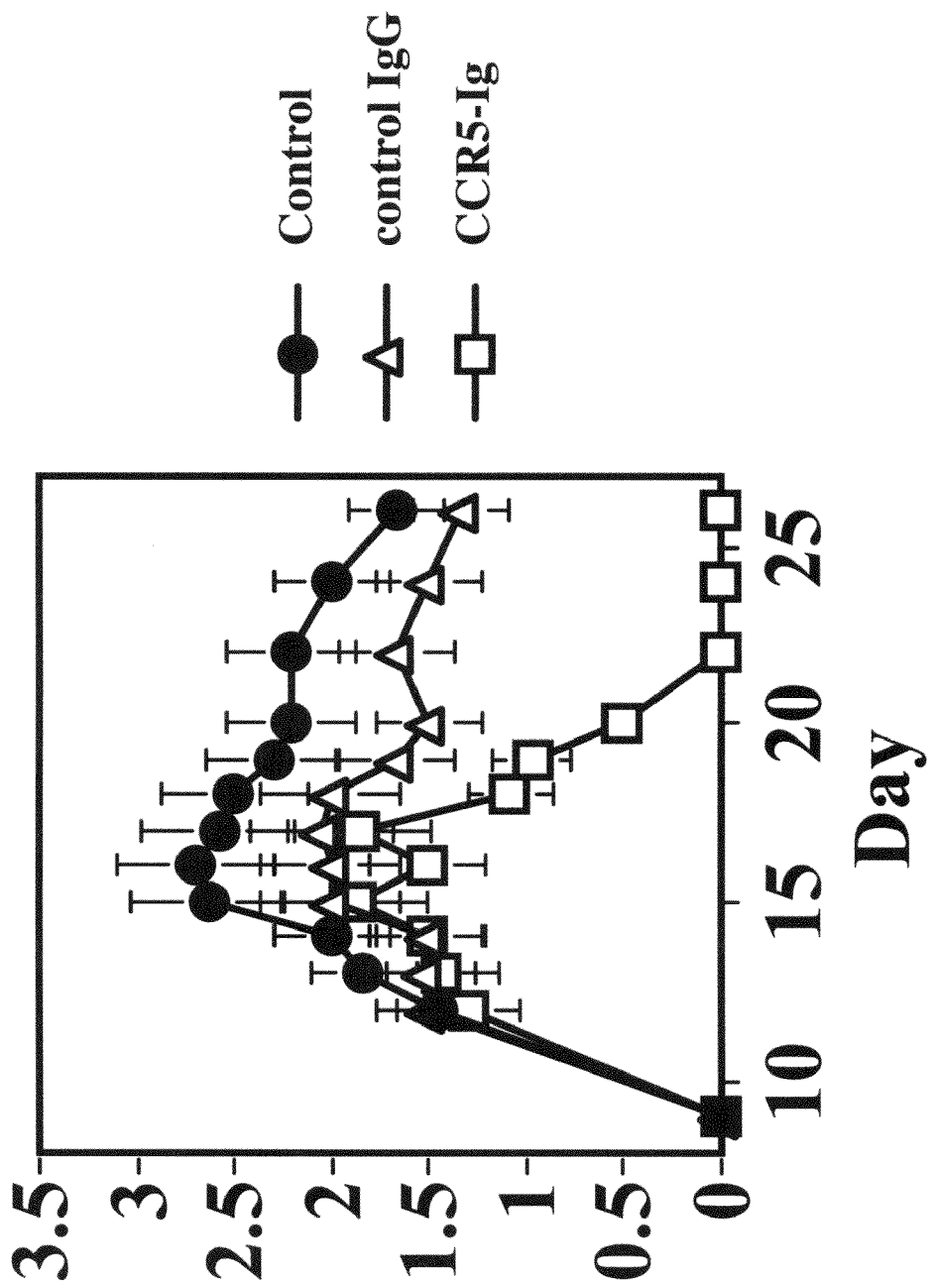

FIG. 7 is a graph depicting the ability of CCR5(EC2)-Ig to suppress ongoing Experimental Autoimmune Encephalomyelitis (EAE) in mice. In brief, three groups of C57/B mice (4 mice in each group) were subjected to active induction of EAE by MOGp35-55. Beginning one day after the onset of disease (day 12), these mice were treated with repeated intravenous administrations (every other day) of 300 μg/mouse of either a CCR5(EC2)-IgG (indicated by squares), isotype matched IgG (indicated by triangles) or with PBS (indicated by circles). An observer blind to the experimental procedure scored EAE daily for clinical manifestation of disease.

Figure 8A:
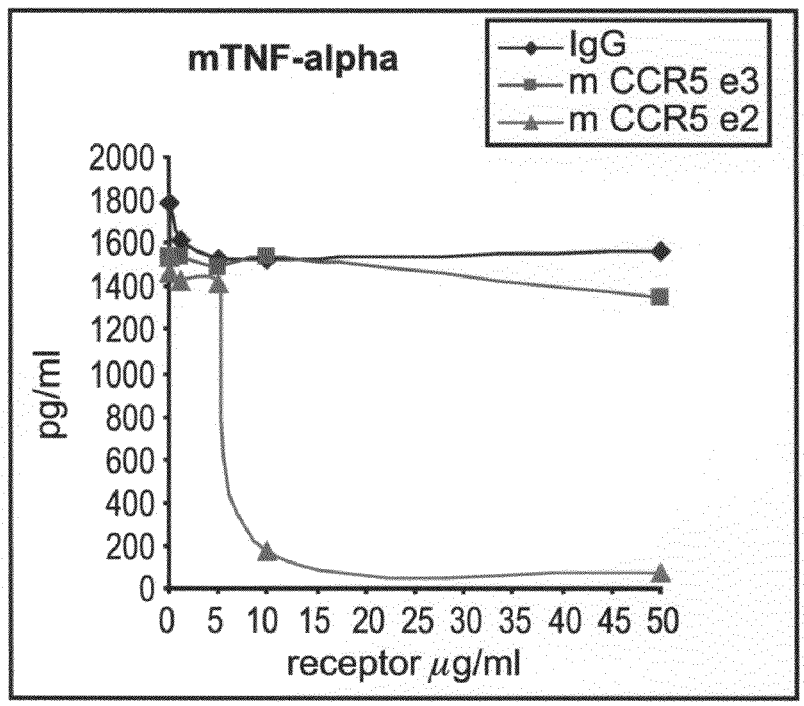
Figure 8B:
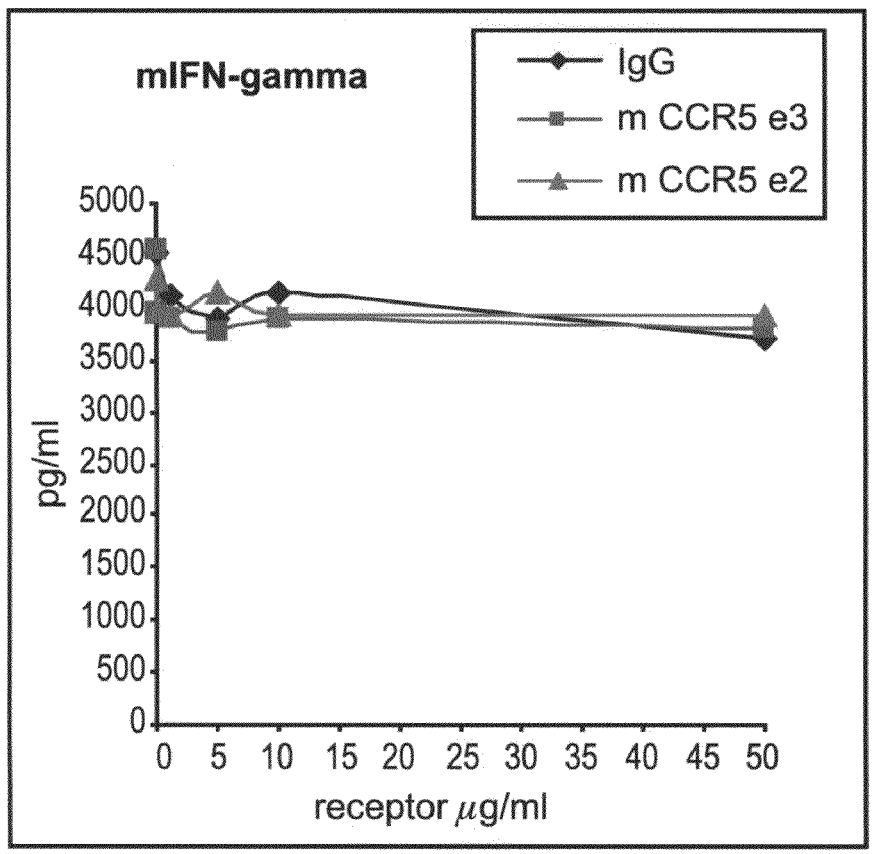
Figure 8C:
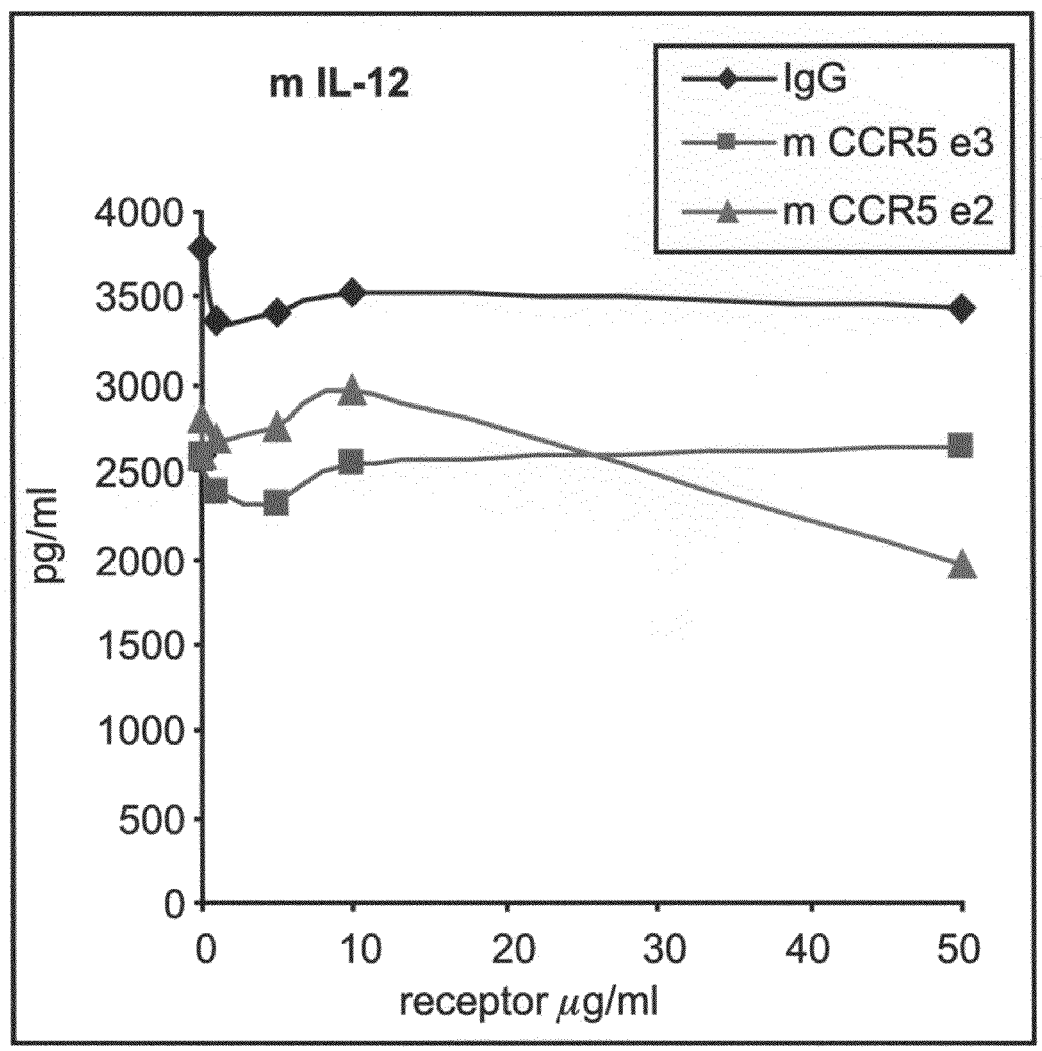

FIGS. 8A-C are graphs depicting the ability of mCCR5-Ig to alter in-vitro cytokine secretion by EAE derived splenocytes. In brief, three groups of C57/B mice (4 mice in each group) were subjected to active induction of EAE by MOGp35-55. On day 9 the splenocytes were harvested and were restimulated for 72 hours with 50 µg/ml MOGp35-55 along with different concentrations of isotype matched IgG (mIgG) (indicated by diamonds), control CCR5 [CCR5 (EC3)-IgG (indicated by squares)] or CCR5(EC2)-IgG (indicated by triangles). The supernatants were analyzed by ELISA for cytokine production. FIG. 8A is a graph showing TNF-α secretion by EAE derived splenocytes. FIG. 8B is a graph showing IFN-γ secretion by EAE derived splenocytes. FIG. 8C is a graph showing IL-12 secretion by EAE derived splenocytes.

DESCRIPTION OF THE PREFERRED EMBODIMENTS

The present invention is of soluble molecules and pharmaceutical compositions which comprise the same for the treatment of CCR5/CCR5-ligand associated diseases, such as autoimmune inflammatory diseases.

The principles and operation of the method according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

CCR5, a member of the C—C chemokine receptors, is expressed on many cell types, including Th1 lymphocytes. Several C—C chemokine ligands, including CCL3 (MIP-1α) and CCL5 (RANTES), bind CCR5. Recently, studies have demonstrated the significance of CCR5 and its ligands in the pathogenesis of inflammatory diseases such as Rheumatoid Arthritis (RA) and Multiple Sclerosis (MS).

The use of neutralizing ligands has been suggested to block CCR5 mediated signaling however, however the use of antibody therapy is implicated with harmful induction of anti idiotypic responses in the host. In addition antibody therapy is inefficient in neutralization of the entire repertoire of CCR5-ligands, allowing the latter to elicit activating signals.

An alternative approach relates to the use of soluble receptors. This approach has been implicated in various publications, however no specific CCR5 molecules were envisaged nor were such ever constructed.

Whilst reducing the present invention to practice, the present inventors have discovered that the extracellular domain 2 (EC2) of CCR5 (amino acid coordinates 165-195 of CCR5 GenBank Accession No. NP_000570; SEQ ID NO: 18 binds CCR5 ligands exclusively with high affinity, whereas the other extracellular domains, EC1 (amino acid coordinates 88-102 of CCR5 GenBank Accession No. NP_000570; SEQ ID NO: 16), EC3 (amino acid coordinates 261-291 of CCR5 GenBank Accession No. NP_000570; SEQ ID NO: 20) and N (amino acid coordinates 1-34 of CCR5 GenBank Accession No. NP_000570; SEQ ID NO: 14), bind CCR5 ligands with extremely low affinity (Example 2 in the examples section below). Thus, it is envisaged that a soluble molecule which comprises the EC2 domain of CCR5 can be used for treating CCR5 associated diseases by seizing explicitly CCR5 ligands (e.g., CCL3, CCL4 and CCL5). Soluble decoy proteins generated according to the teachings of the present invention are sufficiently active, small and bioavailable for use in human therapy.

As is illustrated herein below and the Examples section which follows, the present inventors have constructed human and mouse soluble CCR5 fusion polypeptides and expressed them in eukaryotic cell systems (see Example 1 of the Examples section which follows). Exclusive affinity of the CCR5-EC2 domain to various CCR5 ligands was demonstrated in Examples 2-3. Cross-reactivity between mouse CCR5-EC2 and human CCR5 ligands was demonstrated by ELISA (see Example 4). Molecules generated according to the teachings of the present invention were proven functional as was manifested by inhibition of CCR5 ligand-induced cell migration (see Examples 5 and 6). These results were further substantiated in vivo by suppressing ongoing encephalomyelitis (see Example 7) and ex vivo by suppressing the production of pro-inflammatory cytokines in EAE (see Example 8).

Taken together the present teachings portray a therapeutic value to the soluble molecules of the present invention.

Thus, the present invention envisages the use of any CCR5 amino acid sequence which comprises the EC2 domain of CCR5 and preferably devoid of an N-terminus domain of CCR5, and/or compositions comprising same for the treatment of CCR5/CCR5-ligands associated diseases, such as MS. Importantly, compositions of the present invention are non-immunogenic to achieve maximal therapeutic efficacy. Thus, the present invention envisages for example, inclusion of the CCR5 sequence in a complex where it is attached to a proteinaceous (e.g., heterologous amino acid sequence) or non-proteinaceous moieties (e.g., PEG), each of which being capable of prolonging the half-life of the composition in the circulation.

Thus, according to one aspect of the present invention there is provided a soluble molecule comprising a heterologous amino acid sequence conjugated to a CCR5 amino acid sequence being capable of binding a CCR5 ligand, and wherein the molecule is devoid of an N-terminus domain of CCR5.

As used herein the term "soluble" refers to the ability of the molecules of the present invention to dissolve in a physiological aqueous solution (pH about 7, e.g., solubility level in aqueous media of >100 µg/ml) without substantial aggregation.

As used herein the phrase "CCR5 amino acid sequence" refers to a peptide portion of a mammalian (e.g., human) chemokine C—C receptor 5 protein having binding affinity for CCR5 ligands. It should be noted that a single CCR5 amino acid sequence may be included in the molecules of the present invention, but inclusion of at least two CCR5 amino acid sequences (e.g., of similar affinity), each being capable of binding CCR5 (preferably with high affinity) may be preferred. Due to increased avidity, these polypeptides may be used as potent inhibitors of CCR5 ligand activity and lower dosages may be administered. An example of a CCR5 amino acid sequence is set forth in GenBank Accession No. NP_000570 (encoded by GenBank Accession No.

NM_000579); or GenBank Accession No. NP_034047 (encoded by GenBank Accession No. NM_009917).

A CCR5 amino acid sequence of the present invention comprises the EC2 domain of the receptor but is preferably devoid of the amino terminus (N-ter) part of the receptor (see designations for human and mouse domains according to Table 1 below). As shown in Example 2 of the Examples section which follows, binding of CCR5 to its ligands is mediated by the EC2 domain alone while the N-ter and EC3 domains play only a negligible role in ligand binding In addition to the above, the peptides of the present invention may also include one or more modified amino acids or one or more non-amino acid monomers (e.g., fatty acids, complex carbohydrates, etc.).

The term "amino acid" or "amino acids" is understood to include the 20 naturally occurring amino acids; those amino acids often modified post-translationally in vivo, including, for example, hydroxyproline, phosphoserine, and phosphothreonine; and other less common amino acids, including but not limited to 2-aminoadipic acid, hydroxylysine, isodesmo-

TABLE 1

| | MOUSE | | HUMAN | |
|---|---|---|---|---|
| | Nucleic acid coordinates on mCCR5 GenBank Accession No. NM_009917/SEQ ID NO | Amino acid coordinates on mCCR5 GenBank Accession No. NP_034047/SEQ ID NO | Nucleic acid coordinates on hCCR5 GenBank Accession No. NM_000579/SEQ ID NO | Amino acid coordinates on hCCR5 GenBank Accession No. NP_000570/SEQ ID NO |
| N-ter | 1-81 | 1-27 | 1-102 | 1-34 |
| | 5 | 6 | 13 | 14 |
| EC1 | 271-336 | 91-112 | 262-306 | 88-102 |
| | 7 | 8 | 15 | 16 |
| EC2 | 508-597 | 170-199 | 493-585 | 165-195 |
| | 9 | 10 | 17 | 18 |
| EC3 | 790-864 | 264-288 | 781-843 | 261-291 |
| | 11 | 12 | 19 | 20 |

As used herein "binding affinity" refers to a minimal $K_D$ value of at least $10^{-6}$ M., $10^{-7}$ M, $10^{-8}$ M, $10^{-9}$ M, $10^{-10}$ M . . . .

The term "peptide" as used herein encompasses native peptides (either degradation products, synthetically synthesized peptides, or recombinant peptides), peptidomimetics (typically, synthetically synthesized peptides), and the peptide analogues peptoids and semipeptoids, and may have, for example, modifications rendering the peptides more stable while in a body or more capable of penetrating into cells. Such modifications include, but are not limited to: N-terminus modifications; C-terminus modifications; peptide bond modifications, including but not limited to $CH_2$—NH, $CH_2$—S, $CH_2$—S=O, O=C—NH, $CH_2$—O, $CH_2$—$CH_2$, S=C—NH, CH=CH, and CF=CH; backbone modifications; and residue modifications. Methods for preparing peptidomimetic compounds are well known in the art and are specified, for example, in Ramsden, C. A., ed. (1992), Quantitative Drug Design, Chapter 17.2, F. Choplin Pergamon Press, which is incorporated by reference as if fully set forth herein. Further details in this respect are provided hereinbelow.

Peptide bonds (—CO—NH—) within the peptide may be substituted, for example, by N-methylated bonds (—N(CH3)—CO—); ester bonds (—C(R)H—C—O—O—C(R)—N—); ketomethylene bonds (—CO—CH2-); α-aza bonds (—NH—N(R)—CO—), wherein R is any alkyl group, e.g., methyl; carba bonds (—CH2-NH—); hydroxyethylene bonds (—CH(OH)—CH2-); thioamide bonds (—CS—NH—); olefinic double bonds (—CH=CH—); retro amide bonds (—NH—CO—); and peptide derivatives (—N(R)—CH2-CO—), wherein R is the "normal" side chain, naturally presented on the carbon atom. These modifications can occur at any of the bonds along the peptide chain and even at several (2-3) at the same time.

Natural aromatic amino acids, Trp, Tyr, and Phe, may be substituted for synthetic non-natural acids such as, for instance, tetrahydroisoquinoline-3-carboxylic acid (TIC), naphthylelanine (Nol), ring-methylated derivatives of Phe, halogenated derivatives of Phe, and o-methyl-Tyr.

sine, nor-valine, nor-leucine, and ornithine. Furthermore, the term "amino acid" includes both D- and L-amino acids.

Tables 2 and 3 below list naturally occurring amino acids (Table 2) and non-conventional or modified amino acids (Table 3) which can be used with the present invention.

TABLE 2

| Amino Acid | Three-Letter Abbreviation | One-letter Symbol |
|---|---|---|
| alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| glycine | Gly | G |
| Histidine | His | H |
| isoleucine | Iie | I |
| leucine | Leu | L |
| Lysine | Lys | K |
| Methionine | Met | M |
| phenylalanine | Phe | F |
| Proline | Pro | P |
| Serine | Ser | S |
| Threonine | Thr | T |
| tryptophan | Trp | W |
| tyrosine | Tyr | Y |
| Valine | Val | V |
| Any amino acid as above | Xaa | X |

TABLE 3

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylyethyl) glycine | Nhtrp |
| D-N-methyllysine | Dnmlys | N-methyl-γ-aminobutyrate | Nmgabu |
| N-methylcyclohexylalanine | Nmchex | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |

TABLE 3-continued

| Non-conventional amino acid | Code | Non-conventional amino acid | Code |
|---|---|---|---|
| D-N-methylisoleucine | Dnmile | N-(imidazolylethyl)glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchex | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α-methylvaline | Mtrp | L-α-methyltyrosine | Mtyr |
| L-α-methylleucine | Mval Nnbhm | L-N-methylhomophenylalanine | Nmhphe |
| N-(N-(2,2-diphenylethyl) carbamylmethyl-glycine | Nnbhm | N-(N-(3,3-diphenylpropyl) carbamylmethyl(1)glycine | Nnbhe |
| 1-carboxy-1-(2,2-diphenyl ethylamino)cyclopropane | Nmbc | | |

The peptides of the present invention are preferably utilized in a linear form, although it will be appreciated that in cases where cyclization does not severely interfere with peptide characteristics, cyclic forms of the peptide can also be utilized.

Generation of peptide mimetics, as described hereinabove, can be effected using various approaches, including, for example, display techniques.

Thus, the present invention contemplates a display library comprising a plurality of display vehicles (such as phages, viruses or bacteria) each displaying at least 5, at least 7, at least 11, at least 15, at least 20, at least 25 consecutive amino acids derived from polypeptide sequences of the EC2 of CCR5 (e.g., SEQ ID NO: 10 or 18).

Methods of constructing such display libraries are well known in the art. Such methods are described in, for example, Young A C, et al., "The three-dimensional structures of a polysaccharide binding antibody to *Cryptococcus neoformans* and its complex with a peptide from a phage display library: implications for the identification of peptide mimotopes" J Mol Biol 1997 Dec. 12; 274(4):622-34; Giebel LB et al. "Screening of cyclic peptide phage libraries identifies ligands that bind streptavidin with high affinities" Biochemistry 1995 Nov. 28; 34(47):15430-5; Davies E L et al., "Selection of specific phage-display antibodies using libraries derived from chicken immunoglobulin genes" J Immunol Methods 1995 Oct. 12; 186(1):125-35; Jones C R T al. "Current trends in molecular recognition and bioseparation" J Chromatogr A 1995 Jul. 14; 707(1):3-22; Deng S J et al. "Basis for selection of improved carbohydrate-binding single-chain antibodies from synthetic gene libraries" Proc Natl Acad Sci USA 1995 May 23; 92(11):4992-6; and Deng S J et al. "Selection of antibody single-chain variable fragments with improved carbohydrate binding by phage display" J Biol Chem 1994 Apr. 1; 269(13):9533-8, which are incorporated herein by reference.

Peptide mimetics can also be uncovered using computational biology. Software programs useful for displaying three-dimensional structural models, such as RIBBONS (Carson, M., 1997. Methods in Enzymology 277, 25), O (Jones, TA. et al., 1991. Acta Crystallogr. A47, 110), DINO (DINO: Visualizing Structural Biology (2001) www(dot)dino3d(dot)org); and QUANTA, INSIGHT, SYBYL, MACROMODE, ICM, MOLMOL, RASMOL and GRASP (reviewed in Kraulis, J., 1991. Appl Crystallogr. 24, 946) can be utilized to model interactions between MCP-1 and prospective peptide mimetics to thereby identify peptides which display the highest probability of binding to a specific MCP-1 region. Computational modeling of protein-peptide interactions has been successfully used in rational drug design, for further detail, see Lam et al., 1994. Science 263, 380; Wlodawer et al., 1993. Ann Rev Biochem. 62, 543; Appelt, 1993. Perspectives in Drug Discovery and Design 1, 23; Erickson, 1993. Perspectives in Drug Discovery and Design 1, 109, and Mauro MJ. et al., 2002. J Clin Oncol. 20, 325-34.

As mentioned the chimeric molecule of this aspect of the present invention includes a heterologous amino acid sequence.

As used herein the phrase "heterologous amino acid sequence" refers to a non-immunogenic amino acid sequence which does not form a part of the CCR5 amino acid sequence. This sequence preferably confers solubility to the molecule of this aspect of the present invention, preferably increasing the half-life of the chimeric molecule in the serum.

The heterologous amino acid sequence is generally localized at the amino- or carboxyl-terminus of the CCR5 peptide of the present invention.

As mentioned, the at least one heterologous amino acid sequence can be conjugated to the CCR5 amino acid sequence of the present invention. For example, the at least one CCR5 amino acid sequence may be embedded between two heterologous sequences, such as described Hoogenboom (1991) Mol. Immunol. 28:1027-1037. The heterologous amino acid sequence may be attached to the CCR5 amino acid sequence by any of peptide or non-peptide bond. Attachment of the CCR5 amino acid sequence to the heterologous amino acid sequence may be effected by direct covalent bonding (peptide bond or a substituted peptide bond) or indirect binding such as by the use of a linker having functional groups. Functional groups include, without limitation, a free carboxylic acid (C(=O)OH), a free amino group (NH$_2$), an ester group (C(=O)OR, where R is alkyl, cycloalkyl or aryl), an acyl halide group (C(=O)A, where A is fluoride, chloride, bromide or iodide), a halide (fluoride, chloride, bromide or iodide), a hydroxyl group (OH), a thiol group (SH), a nitrile group (C≡N), a free C-carbamic group (NR"—C(=O)—OR', where each of R' and R" is independently hydrogen, alkyl, cycloalkyl or aryl).

An example of a heterologous amino acid sequence which may be used in accordance with this aspect of the present invention is an immunoglobulin amino acid sequence, such as the hinge and Fc regions of an immunoglobulin heavy domain (see U.S. Pat. No. 6,777,196). The immunoglobulin moiety in the chimeras of this aspect of the present invention may be obtained from IgG1, IgG2, IgG3 or IgG4 subtypes, IgA, IgE, IgD or IgM, as further discussed hereinbelow.

Chimeras constructed from a receptor sequence linked to an appropriate immunoglobulin constant domain sequence (immunoadhesins) are known in the art. Immunoadhesins reported in the literature include fusions of the T cell receptor [Gascoigne et al., Proc. Natl. Acad. Sci. USA, 84: 2936-2940 (1987)]; CD4 [Capon et al., Nature 337: 525-531 (1989); Traunecker et al., Nature, 339: 68-70 (1989); Zettmeissl et al., DNA Cell Biol. USA, 9: 347-353 (1990); Byrn et al., Nature, 344: 667-670 (1990)]; L-selectin (homing receptor) [(Watson et al., J. Cell. Biol., 110:2221-2229 (1990); Watson et al., Nature, 349: 164-167 (1991)]; CD44 [Aruffo et al., Cell, 61: 1303-1313 (1990)]; CD28 and B7 (Linsley et al., J. Exp. Med., 173: 721-730 (1991)]; CTLA-4 [Lisley et al., J. Exp. Med. 174: 561-569 (1991)]; CD22 [Stamenkovic et al., Cell, 66:1133-1144 (1991)]; TNF receptor [Ashkenazi et al., Proc. Natl. Acad. Sci. USA, 88: 10535-10539 (1991); Lesslauer et al., Eur. J. Immunol., 27: 2883-2886 (1991); Peppel et al., J. Exp. Med., 174:1483-1489 (1991)]; NP receptors [Bennett et al., J. Biol. Chem. 266:23060-23067 (1991)]; and IgE receptor a [Ridgway et al., J. Cell. Biol., 1 15: abstr. 1448 (1991)].

Typically, in such fusions the chimeric molecule will retain at least functionally active hinge and CH2 and CH3 domains of the constant region of an immunoglobulin heavy chain. Fusions can also be generated to the C-terminus of the Fc portion of a constant domain, or immediately N-terminal to the CH1 of the heavy chain or the corresponding region of the light chain.

The exact site at which fusion (conjugation) between the heterologous sequence and the CCR5 amino acid sequence is not critical. Particular sites are well known in the art and may be selected in order to optimize the biological activity, secretion or binding characteristics of the chimeric molecules of this aspect of the present invention (see Example 1 of the Example section which follows).

Though it may be possible to conjugate the entire heavy chain constant region to the CCR5 amino acid sequence of the present invention, it is preferable to fuse shorter sequences. For example, a sequence beginning in the hinge region just upstream of the papain cleavage site, which defines IgG Fc chemically; residue 216, taking the first residue of heavy chain constant region to be 114, or analogous sites of other immunoglobulins, is used in the fusion. In a particularly preferred embodiment, the CCR5 amino acid sequence is fused to the hinge region and CH2 and CH3, or to the CH1, hinge, CH2 and CH3 domains of an IgG1, IgG2, or IgG3 heavy chain (see U.S. Pat. No. 6,777,196). The precise site at which the fusion is made is not critical, and the optimal site can be determined by routine experimentation.

As mentioned, the immunoglobulin sequences used in the construction of the chimeric molecules of this aspect of the present invention may be from an IgG immunoglobulin heavy chain constant domain. The use of human IgG1 and IgG3 immunoglobulin sequences is preferred (e.g., as set forth in SEQ ID NOs. 21, 22, 25 and 26). A major advantage of using IgG1 is that IgG1 can be purified efficiently on immobilized protein A. In contrast, purification of IgG3 requires protein G, a significantly less convenient medium. However, other structural and functional properties of immunoglobulins should be considered when choosing the Ig fusion partner for a particular chimera construction. For example, the IgG3 hinge is longer and more flexible, so it can accommodate larger CCR5 amino acid sequences that may not fold or function properly when fused to IgG1. Another consideration may be valency; IgG are bivalent homodimers, whereas Ig subtypes like IgA and IgM may give rise to dimeric or pentameric structures, respectively, of the basic Ig homodimer unit. Other considerations in selecting the immunoglobulin portion of the chimeric molecules of this aspect of the present invention are described in U.S. Pat. No. 6, 77,196.

Further examples of heterologous amino acid sequences commonly used in fusion protein construction include, but are not limited to galactosidase, glucuronidase, glutathione-S-transferase (GST), carboxy terminal peptide (CTP) from chorionic gonadotrophin (CGβ) and chloramphenicol acetyltransferase (CAT).

As used herein the phrase "CCR5 ligand" refers any molecule which binds with a minimal affinity of $K_D=10^{-6}$ M to CCR5 and activates signaling therefrom (e.g., pro-inflammatory cytokine production). Examples include soluble or non-soluble natural or synthetic chemokine ligands as well as infectious agents having a trophism for CCR5 positive cells [e.g., viruses such as HIV (Princen and Schols, Cytok Growth Factor Rev. (2005) 16(6):659-77)]. Examples of CCR5 chemokine ligands include, but are not limited to, C—C chemokines such as CCL2 (MCP-1), CCL3 (MIP-1α), CCL4 (MIP-1β), CCL5 (RANTES), CCL11 (eotaxin) and CCL16 [Blanpain et al., Blood. (1999) 94:1899-905; Nomiyama et al., Int Immunol (2001) (8):1021-9].

According to a preferred embodiment of this aspect of the present invention, the soluble molecule of this aspect of the present invention is as set forth in SEQ ID NO: 2 or 4.

Thus, molecules of this aspect of the present invention may comprise heterologous amino acid sequences, as described above.

Additionally or alternatively as mentioned hereinabove CCR5 amino acid sequences of the present invention may be attached to a non-proteinaceous moiety, such molecules are preferably selected non-immunogenic in a subject.

Thus, according to another aspect of the present invention, there is provided a soluble molecule comprising a CCR5 amino acid sequence (as described above) attached to a non-proteinaceous moiety, wherein the CCR5 amino acid sequence is capable of binding a CCR5 ligand and whereas the molecule is non-immunogenic in a subject.

Such a molecule is highly stable (resistant to in-vivo proteaolytic activity probably due to steric hindrance conferred by the non-proteinaceous moiety) and may be produced using common solid phase synthesis methods which are inexpensive and highly efficient, as further described hereinbelow. However, it will be appreciated that recombinant techniques may still be used, whereby the recombinant peptide product is subjected to in-vitro modification (e.g., PEGylation as further described hereinbelow).

The phrase "non-proteinaceous moiety" as used herein refers to a molecule not including peptide bonded amino acids that is attached to the above-described CCR5 amino acid sequence. According to presently preferred embodiments the non-proteinaceous moiety of this aspect of the present invention is a polymer or a co-polymer (synthetic or natural). Non-limiting examples of the non-proteinaceous moiety of the present invention include polyethylene glycol (PEG), Polyvinyl pyrrolidone (PVP), divinyl ether and maleic anhydride copolymer (DIVEMA; see for example, Kaneda Y, et al., 1997, Biochem. Biophys. Res. Commun. 239: 160-5) and poly(styrene comaleic anhydride) (SMA; see for example, Mu Y, et al., 1999, Biochem Biophys Res Commun. 255: 75-9).

It will be appreciated that such non-proteinaceous moieties may be also attached to the above mentioned fusion molecules (i.e., which comprise a heterologous amino acid sequence) to promote stability and possibly solubility of the molecules.

Bioconjugation of such a non-proteinaceous moiety confers the CCR5 amino acid sequence with stability (e.g., against protease activities) and/or solubility (e.g., within a biological fluid such as blood, digestive fluid) while preserving its biological activity and prolonging its half-life. Bioconjugation is advantageous particularly in cases of therapeutic proteins which exhibit short half-life and rapid clearance from the blood. The increased half-lives of bioconjugated proteins in the plasma results from increased size of protein conjugates (which limits their glomerular filtration) and decreased proteolysis due to polymer steric hindrance. Generally, the more polymer chains attached per peptide, the greater the extension of half-life. However, measures are taken not to reduce the specific activity of the CCR5 amino acid sequence of the present invention (i.e., CCR5 ligand binding).

Bioconjugation of the CCR5 amino acid sequence with PEG (i.e., PEGylation) can be effected using PEG derivatives such as N-hydroxysuccinimide (NHS) esters of PEG carboxylic acids, monomethoxyPEG$_2$—NHS, succinimidyl ester of carboxymethylated PEG (SCM-PEG), benzotriazole carbonate derivatives of PEG, glycidyl ethers of PEG, PEG p-nitrophenyl carbonates (PEG-NPC, such as methoxy PEG-NPC), PEG aldehydes, PEG-orthopyridyl-disulfide, carbonyldimidazol-activated PEGs, PEG-thiol, PEG-maleimide. Such PEG derivatives are commercially available at various molecular weights [See, e.g., Catalog, Polyethylene Glycol and Derivatives, 2000 (Shearwater Polymers, Inc., Huntsvlle, Ala.)]. If desired, many of the above derivatives are available in a monofunctional monomethoxyPEG (mPEG) form. In general, the PEG added to the CCR5 amino acid sequence of the present invention should range from a molecular weight (MW) of several hundred Daltons to about 100 kDa (e.g., between 3-30 kDa). Larger MW PEG may be used, but may result in some loss of yield of PEGylated peptides. The purity of larger PEG molecules should be also watched, as it may be difficult to obtain larger MW PEG of purity as high as that obtainable for lower MW PEG. It is preferable to use PEG of at least 85% purity, and more preferably of at least 90% purity, 95% purity, or higher. PEGylation of molecules is further discussed in, e.g., Hermanson, Bioconjugate Techniques, Academic Press San Diego, Calif. (1996), at Chapter 15 and in Zalipsky et al., "Succinimidyl Carbonates of Polyethylene Glycol," in Dunn and Ottenbrite, eds., Polymeric Drugs and Drug Delivery Systems, American Chemical Society, Washington, D.C. (1991).

Conveniently, PEG can be attached to a chosen position in the CCR5 amino acid sequence by site-specific mutagenesis as long as the activity of the conjugate is retained (i.e., CCR5 ligand binding). A target for PEGylation could be any Cysteine residue at the N-terminus or the C-terminus of the CCR5 amino acid sequence. Additionally or alternatively, other Cysteine residues can be added to the CCR5 amino acid sequence (e.g., at the N-terminus or the C-terminus) to thereby serve as a target for PEGylation. Computational analysis may be effected to select a preferred position for mutagenesis without compromising the activity.

Various conjugation chemistries of activated PEG such as PEG-maleimide, PEG-vinylsulfone (VS), PEG-acrylate (AC), PEG-orthopyridyl disulfide can be employed. Methods of preparing activated PEG molecules are known in the arts. For example, PEG-VS can be prepared under argon by reacting a dichloromethane (DCM) solution of the PEG-OH with NaH and then with di-vinylsulfone (molar ratios: OH 1: NaH 5: divinyl sulfone 50, at 0.2 gram PEG/mL DCM). PEG-AC is made under argon by reacting a DCM solution of the PEG-OH with acryloyl chloride and triethylamine (molar ratios: OH 1: acryloyl chloride 1.5: triethylamine 2, at 0.2 gram PEG/mL DCM). Such chemical groups can be attached to linearized, 2-arm, 4-arm, or 8-arm PEG molecules.

While conjugation to cysteine residues is one convenient method by which the CCR5 amino acid of the present invention can be PEGylated, other residues can also be used if desired. For example, acetic anhydride can be used to react with $NH_2$ and SH groups, but not COOH, S—S, or —$SCH_3$ groups, while hydrogen peroxide can be used to react with —SH and —$SCH_3$ groups, but not $NH_2$. Reactions can be conducted under conditions appropriate for conjugation to a desired residue in the peptide employing chemistries exploiting well-established reactivities.

For bioconjugation of the CCR5 amino acid sequence of the present invention with PVP, the terminal COOH-bearing PVP is synthesized from N-vinyl-2-pyrrolidone by radical polymerization in dimethyl formamide with the aid of 4,4'-azobis-(4-cyanovaleric acid) as a radical initiator, and 3-mercaptopropionic acid as a chain transfer agent. Resultant PVPs with an average molecular weight of Mr 6,000 can be separated and purified by high-performance liquid chromatography and the terminal COOH group of synthetic PVP is activated by the N-hydroxysuccinimide/dicyclohexyl carbodiimide method. The CCR5 amino acid sequence is reacted with a 60-fold molar excess of activated PVP and the reaction is stopped with amino caploic acid (5-fold molar excess against activated PVP), essentially as described in Haruhiko Kamada, et al., 2000, Cancer Research 60: 6416-6420, which is fully incorporated herein by reference.

Resultant conjugated CCR5 molecules (e.g., PEGylated or PVP-conjugated CCR5) are separated, purified and qualified using e.g., high-performance liquid chromatography (HPLC). In addition, purified conjugated molecules of this aspect of the present invention may be further qualified using e.g., in vitro assays in which the binding specificity of CCR5 ligand to its receptor (e.g., CCR5) is tested in the presence or absence of the CCR5 conjugates of the present invention, essentially as described for other chemokines [e.g., MIP-1α, see for example, Hesselgesser J, 1998 (Supra), which is fully incorporated herein by reference].

Molecules of this aspect of present invention can be biochemically synthesized such as by using standard solid phase techniques. These methods include exclusive solid phase synthesis, partial solid phase synthesis methods, fragment condensation and classical solution synthesis. These methods are preferably used when the peptide is relatively short (i.e., 10 kDa) and/or when it cannot be produced by recombinant techniques (i.e., not encoded by a nucleic acid sequence, such as a "Tag" further described hereinbelow) and therefore involve different chemistry.

Solid phase peptide synthesis procedures are well known in the art and further described by John Morrow Stewart and Janis Dillaha Young, Solid Phase Peptide Syntheses (2nd Ed., Pierce Chemical Company, 1984).

Synthetic peptides can be purified by preparative high performance liquid chromatography [Creighton T. (1983) Proteins, structures and molecular principles. WH Freeman and Co. N.Y.] and the composition of which can be confirmed via amino acid sequencing.

In cases where large amounts of the peptides of the present invention are desired, the peptides of the present invention can be generated using recombinant techniques such as described by Bitter et al. (1987) Methods in Enzymol. 153: 516-544; Studier et al. (1990) Methods in Enzymol. 185:60-89; Brisson et al. (1984) Nature 310:511-514; Takamatsu et al. (1987) EMBO J. 6:307-311; Coruzzi et al. (1984) EMBO J. 3:1671-1680; Brogli et al. (1984) Science 224:838-843; Gurley et al. (1986) Mol. Cell. Biol. 6:559-565 and Weissbach & Weissbach, 1988&, Methods for Plant Molecular Biology, Academic Press, NY, Section VIII, pp 421-463.

Briefly, an expression construct (i.e., expression vector), which includes an isolated polynucleotide (i.e., isolated from a naturally occurring source thereof, e.g., SEQ ID NO: 1, 3, 9, 17) which comprises a nucleic acid sequence encoding the CCR5 amino acid sequence (optionally in frame fused to a nucleic acid sequence encoding the heterologous amino acid sequence e.g., SEQ ID NO: 21 or 25) of the present invention positioned under the transcriptional control of a regulatory element, such as a promoter, is introduced into host cells.

For example, a nucleic acid sequence encoding a CCR5 peptide of the present invention (e.g., SEQ ID NO: 9 or 17) is ligated in frame to an immunoglobulin cDNA sequence (e.g., SEQ ID NO: 21 or 25). It will be appreciated that, ligation of genomic immunoglobulin fragments can also be used. In this case, fusion requires the presence of immunoglobulin regulatory sequences for expression. cDNAs encoding IgG heavy-chain constant regions can be isolated based on published sequence from cDNA libraries derived from spleen or peripheral blood lymphocytes, by hybridization or by polymerase chain reaction (PCR) techniques. The nucleic acid sequences encoding the CCR5 amino acid sequence and immunoglobulin can be ligated in tandem into an expression construct (vector) that directs efficient expression in the selected host cells, further described hereinbelow. For expression in mammalian cells, pRK5-based vectors [Schall et al., Cell, 61:361-370 (1990)]; and CDM8-based vectors [Seed, Nature, 329: 840 (1989)] can be used. The exact junction can be created by removing the extra sequences between the designed junction codons using oligonucleotide-directed deletional mutagenesis [Zoller et al, Nucleic Acids Res., 10:6487 (1982); Capon et al., Nature, 337:525-531 (1989)]. Synthetic oligonucleotides can be used, in which each half is complementary to the sequence on either side of the desired junction; ideally, these are 11 to 48-mers. Alternatively, PCR techniques can be used to join the two parts of the molecule in-frame with an appropriate vector.

Methods of introducing the expression construct into a host cell are well known in the art and include, electroporation, lipofection and chemical transformation (e.g., calcium phosphate). See also Example 1 of the Examples section which follows.

The "transformed" cells are cultured under suitable conditions, which allow the expression of the chimeric molecule encoded by the nucleic acid sequence.

Following a predetermined time period, the expressed chimeric molecule is recovered from the cell or cell culture, and purification is effected according to the end use of the recombinant polypeptide.

Depending on the host/vector system utilized, any of a number of suitable transcription and translation elements including constitutive and inducible promoters, transcription enhancer elements, transcription terminators, and the like, can be used in the expression vector [see, e.g., Bitter et al., (1987) Methods in Enzymol. 153:516-544].

Other than containing the necessary elements for the transcription and translation of the inserted coding sequence (encoding the chimera), the expression construct of the present invention can also include sequences engineered to optimize stability, production, purification, yield or toxicity of the expressed fusion protein.

A variety of prokaryotic or eukaryotic cells can be used as host-expression systems to express the fusion protein coding sequence. These include, but are not limited to, microorganisms, such as bacteria transformed with a recombinant bacteriophage DNA, plasmid DNA or cosmid DNA expression vector containing the chimera coding sequence; yeast transformed with recombinant yeast expression vectors containing the chimera coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the chimera coding sequence. Mammalian expression systems are preferably used to express the chimera of the present invention.

The choice of host cell line for the expression of the molecules depends mainly on the expression vector. Eukaroyotic exoression systems are preferred (e.g., mammalian and insects) since they allow post translational modifications (e.g., glyccosylation). Another consideration is the amount of protein that is required. Milligram quantities often can be produced by transient transfections. For example, the adenovirus EIA-transformed 293 human embryonic kidney cell line can be transfected transiently with pRK5-based vectors by a modification of the calcium phosphate method to allow efficient expression. CDM8-based vectors can be used to transfect COS cells by the DEAE-dextran method (Aruffo et al., Cell, 61:1303-1313 (1990); Zettmeissl et al., DNA Cell Biol. US, 9:347-353 (1990)]. If larger amounts of protein are desired, the molecules can be expressed after stable transfection of a host cell line (see Example 1 of the Examples section). It will be appreciated that the presence of a hydrophobic leader sequence at the N-terminus of the molecule will ensure processing and secretion of the molecule by the transfected cells.

It will be appreciated that the use of bacterial or yeast host systems may be preferable to reduce cost of production. However since bacterial host systems are devoid of protein glycosylation mechanisms, a post production glycosylation may be needed.

In any case, transformed cells are cultured under effective conditions, which allow for the expression of high amounts of recombinant polypeptide. Effective culture conditions include, but are not limited to, effective media, bioreactor, temperature, pH and oxygen conditions that permit protein production. An effective medium refers to any medium in which a cell is cultured to produce the recombinant chimera molecule of the present invention. Such a medium typically includes an aqueous. solution having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Depending on the vector and host system used for production, resultant proteins of the present invention may either remain within the recombinant cell, secreted into the fermentation medium, secreted into a space between two cellular membranes, such as the periplasmic space in *E. coli*; or retained on the outer surface of a cell or viral membrane.

Following a predetermined time in culture, recovery of the recombinant protein is effected. The phrase "recovering the recombinant protein" refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

Molecules of the present invention are preferably retrieved in "substantially pure" form. As used herein, "substantially pure" refers to a purity that allows for the effective use of the protein in the applications, described hereinbelow.

Recombinant molecules of the present invention can be conveniently purified by affinity chromatography. The suitability of protein A as an affinity ligand depends on the species and isotype of the immunoglobulin Fc domain that is used in the chimera. Protein A can be used to purify chimeric molecules that are based on human γ1, γ2, or γ4 heavy chains [Lindmark et al., J. Immunol. Meth., 62:1-13 (1983)]. Protein G is preferably used for all mouse isotypes and for human γ3 [Guss et al., EMBO J., 5:1567-1575 (1986)]. The solid support to which the affinity ligand is attached is most often agarose, but other solid supports are also available. Mechanically stable solid supports such as controlled pore glass or poly(styrenedivinyl)benzene allow for faster flow rates and shorter processing times than can be achieved with agarose. The conditions for binding the chimeric molecules to the protein A or G affinity column are dictated entirely by the characteristics of the Fc domain; that is, its species and isotype. Generally, when the proper ligand is chosen, efficient binding occurs directly from unconditioned culture fluid. One distinguishing feature of chimeric molecules of this aspect of the present invention is that, for human .gamma.1 molecules, the binding capacity for protein A is somewhat diminished relative to an antibody of the same Fc type. Bound chimeric molecules of this aspect of the present invention can be efficiently eluted either at acidic pH (at or above 3.0), or in a neutral pH buffer containing a mildly chaotropic salt. This affinity chromatography step can result in a chimeric molecule preparation that is >95% pure. Medical grade purity is essential for therapeutic applications.

Other methods known in the art can be used in place of, or in addition to, affinity chromatography on protein A or G to purify chimeric molecules which include an immunoglobulin portion. Such chimeric molecules behave similarly to antibodies in thiophilic gel chromatography [Hutchens et al., Anal. Biochem., 159:217-226 (1986)] and immobilized metal chelate chromatography [Al-Mashikhi et al., J. Dairy Sci., 71:1756-1763 (1988)]. In contrast to antibodies, however, their behavior on ion exchange columns is dictated not only by their isoelectric points, but also by a charge dipole that may exist in the molecules due to their chimeric nature.

Thus, the present invention provides for numerous configurations of soluble molecules which are capable of binding CCR5 ligands and neutralize signaling therefrom.

The above-described molecules are preferably non-immunogenic for maximizing therapeutic efficacy.

As used herein the term "non-immunogenic" refers a substance which is substantially incapable of producing an immune response in a subject administered therewith. For example, non-immunogenic in a human means that upon contacting the chimeric molecule of this aspect of the present invention with the appropriate tissue of a human, no state of sensitivity or resistance to the chimeric molecule is demonstrable upon the second administration of the chimeric molecule after an appropriate latent period (e.g., 8 to 14 days).

As shown in Example 5 and 6 of the Examples section which follows, the present inventors were able to inhibit CCR5-mediated cell migration and suppress an ongoing immune disease (Example 7) using the molecules of the present invention, substantiating the use of same in therapy.

Thus, according to another aspect of the present invention, there is provided a method of treating a CCR5 and/or CCR5 ligand associated disease in a subject in need thereof. The method comprising administering to the subject a therapeutically effective amount of any of the above-mentioned molecules, thereby treating CCR5 and/or CCR5 ligand associated disease in the subject.

As used herein the term "subject" refers to a mammal, preferably a human subject.

As used herein the term "treating" refers to preventing, curing, reversing, attenuating, alleviating, minimizing, suppressing or halting the deleterious effects of a CCR5 and/or CCR5 ligand associated medical condition.

As used herein the term "CCR5 and/or CCR5 ligand associated medical condition" refers to a medical condition (e.g., disease, syndrome or condition), which depends on the interaction between a CCR5 ligand and CCR5 for onset or progression.

Examples of art references for CCR5 and/or CCR5 ligand associated medical conditions include, but are not limited to, inflammatory diseases, autoimmune diseases, allergic conditions (e.g., asthma), inflammatory bowel diseases (e.g., Crohn's disease and ulcerative colitis), scleroderma, psoriasis, inflammatory dermatoses (e.g., dermatitis), arthritis [e.g., rheumatoid arthritis (Pokorny et al., Ann Rheum Dis (2005) 64:487-490; Wang and Liu, Clin Exp Immunol (2003) 132: 371-8; Nissinen et al., J Rheumatol (2003) 30:1928-34; Mack et al., Arthritis Rheum (1999) 42:981-8)], multiple sclerosis [Zang et al., Brain (2000) 123(9):1874-1882], systemic lupus erythematosus, myasthenia gravis, juvenile onset diabetes, nephritides (e.g., glomerulonephritis), autoimmune thyroiditis, Behcet's disease, cancer (such as with leukocyte infiltration of the skin or organs), certain hematologic malignancies, cytokine-induced toxicity (e.g., septic shock, endotoxic shock), atherosclerosis, immunosuppression (e.g., due to immunodeficiency syndromes such as AIDS), viral diseases [e.g., HIV 1 and 2 (Liu et al., Cell (1996) 86:367-377)].

Various examples of inflammatory diseases which are included in the scope of the present invention include, but are not limited to, As used herein the phrase "inflammatory disorder" includes but is not limited to chronic inflammatory diseases and disorders and acute inflammatory diseases and disorders. Examples of such diseases and conditions are summarized infra.

Inflammatory Diseases Associated with Hypersensitivity

Examples of hypersensitivity include, but are not limited to, Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity and DTH.

Type I or immediate hypersensitivity, such as asthma.

Type II hypersensitivity include, but are not limited to, rheumatoid diseases, rheumatoid autoimmune diseases, rheumatoid arthritis (Krenn V. et al., Histol Histopathol 2000 July; 15 (3):791), spondylitis, ankylosing spondylitis (Jan Voswinkel et al., Arthritis Res 2001; 3 (3): 189), systemic diseases, systemic autoimmune diseases, systemic lupus erythematosus (Erikson J. et al., Immunol Res 1998; 17 (1-2): 49), sclerosis, systemic sclerosis (Renaudineau Y. et al., Clin Diagn Lab Immunol. 1999 March; 6 (2):156); Chan O T. et al., Immunol Rev 1999 June; 169:107), glandular diseases, glandular autoimmune diseases, pancreatic autoimmune diseases, diabetes, Type I diabetes (Zimmet P. Diabetes Res Clin Pract 1996 October; 34 Suppl:S125), thyroid diseases, autoimmune thyroid diseases, Graves' disease (Orgiazzi J. Endocrinol Metab Clin North Am 2000 June; 29 (2):339), thyroiditis, spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), myxedema, idiopathic myxedema (Mitsuma T. Nippon Rinsho. 1999 August; 57 (8): 1759); autoimmune reproductive diseases, ovarian diseases, ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), repeated fetal loss (Tincani A. et al., Lupus 1998;7 Suppl 2:S107-9), neurodegenerative diseases, neurological diseases, neurological autoimmune diseases, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante AJ. And Kraig E, Int Rev Immunol 1999; 18 (1-2):83), motor neuropathies (Kornberg A J. J Clin Neurosci. 2000 May; 7 (3):191), Guillain-Barre syndrome, neuropathies and autoimmune neuropathies (Kusunoki S. Am J Med. Sci. 2000 April; 319 (4):234), myasthenic diseases, Lambert-Eaton myasthenic syndrome (Takamori M. Am J Med. Sci. 2000 April; 319 (4):204), paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydeham chorea, Gilles de la Tourette syndrome, polyendocrinopathies, autoimmune polyendocrinopathies (Antoine J C. and Honnorat J. Rev Neurol (Paris) 2000 January; 156 (1):23); neuropathies, dysimmune neuropathies (Nobile-Orazio E. et al., Electroencephalogr Clin Neurophysiol Suppl 1999; 50:419); neuromyotonia, acquired neuromyotonia, arthrogryposis multiplex congenita (Vincent A. et al., Ann N Y Acad. Sci. 1998 May 13; 841:482), cardiovascular diseases, cardiovascular autoimmune diseases, atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), granulomatosis, Wegener's granulomatosis, arteritis, Takayasu's arteritis and Kawasaki syndrome (Praprotnik S. et al., Wien Klin Wochenschr 2000 Aug. 25; 112 (15-16):660); anti-factor VIII autoimmune disease (Lacroix-Desmazes S. et al., Semin Thromb Hemost. 2000; 26 (2):157); vasculitises, necrotizing small vessel vasculitises, microscopic polyangiitis, Churg and Strauss syndrome, glomerulonephritis, pauci-immune focal necrotizing glomerulonephritis, crescentic glomerulonephritis (Noel L H. Ann Med Interne (Paris). 2000 May; 151 (3):178); antiphospholipid syndrome (Flamholz R. et al., J Clin Apheresis 1999; 14 (4):171); heart failure, agonist-like beta-adrenoceptor antibodies in heart failure (Wallukat G. et al., Am J. Cardiol. 1999 Jun. 17; 83 (12A):75H), thrombocytopenic purpura (Moccia F. Ann Ital Med. Int. 1999 April-June; 14 (2):114); hemolytic anemia, autoimmune hemolytic anemia (Efremov D G. et al., Leuk Lymphoma 1998 January; 28 (3-4):285), gastrointestinal diseases, autoimmune diseases of the gastrointestinal tract, intestinal diseases, chronic inflammatory intestinal disease (Garcia Herola A. et al., Gastroenterol Hepatol. 2000 January; 23 (1):16), celiac disease (Landau Y E. and Shoenfeld Y. Harefuah 2000 Jan. 16; 138 (2):122), autoimmune diseases of the musculature, myositis, autoimmune myositis, Sjogren's syndrome (Feist E. et al., Int Arch Allergy Immunol 2000 September; 123 (1):92); smooth muscle autoimmune disease (Zauli D. et al., Biomed Pharmacother 1999 June; 53 (5-6):234), hepatic diseases, hepatic autoimmune diseases, autoimmune hepatitis (Manns M P. J Hepatol 2000 August; 33 (2):326) and primary biliary cirrhosis (Strassburg C P. et al., Eur J Gastroenterol Hepatol. 1999 June; 11 (6):595).

Type IV or T cell mediated hypersensitivity, include, but are not limited to, rheumatoid diseases, rheumatoid arthritis (Tisch R, McDevitt H O. Proc Natl Acad Sci U S A 1994 Jan. 18; 91 (2):437), systemic diseases, systemic autoimmune diseases, systemic lupus erythematosus (Datta S K., Lupus 1998; 7 (9):591), glandular diseases, glandular autoimmune diseases, pancreatic diseases, pancreatic autoimmune diseases, Type 1 diabetes (Castano L. and Eisenbarth G S. Ann. Rev. Immunol. 8:647); thyroid diseases, autoimmune thyroid diseases, Graves' disease (Sakata S. et al., Mol Cell Endocrinol 1993 March; 92 (1):77); ovarian diseases (Garza K M. et al., J Reprod Immunol 1998 February; 37 (2):87), prostatitis, autoimmune prostatitis (Alexander R B. et al., Urology 1997 December; 50 (6):893), polyglandular syndrome, autoimmune polyglandular syndrome, Type I autoimmune polyglandular syndrome (Hara T. et al., Blood. 1991 Mar. 1; 77 (5):1127), neurological diseases, autoimmune neurological diseases, multiple sclerosis, neuritis, optic neuritis (Soderstrom M. et al., J Neurol Neurosurg Psychiatry 1994 May; 57 (5):544), myasthenia gravis (Oshima M. et al., Eur J Immunol 1990 December; 20 (12):2563), stiff-man syndrome (Hiemstra H S. et al., Proc Natl Acad Sci USA 2001 Mar. 27; 98 (7):3988), cardiovascular diseases, cardiac autoimmunity in Chagas' disease (Cunha-Neto E. et al., J Clin Invest 1996 Oct. 15; 98 (8):1709), autoimmune thrombocytopenic purpura (Semple J W. et al., Blood 1996 May 15; 87 (10):4245), anti-helper T lymphocyte autoimmunity (Caporossi A P. et al., Viral Immunol 1998; 11 (1):9), hemolytic anemia (Sallah S. et al., Ann Hematol 1997 March; 74 (3): 139), hepatic diseases, hepatic autoimmune diseases, hepatitis, chronic active hepatitis (Franco A. et al., Clin Immunol Immunopathol 1990 March; 54 (3):382), biliary cirrhosis, primary biliary cirrhosis (Jones D E. Clin Sci (Colch) 1996

November; 91 (5):551), nephric diseases, nephric autoimmune diseases, nephritis, interstitial nephritis (Kelly C J. J Am Soc Nephrol 1990 August; 1 (2):140), connective tissue diseases, ear diseases, autoimmune connective tissue diseases, autoimmune ear disease (Yoo T J. et al., Cell Immunol 1994 August; 157 (1):249), disease of the inner ear (Gloddek B. et al., Ann N Y Acad Sci 1997 Dec. 29; 830:266), skin diseases, cutaneous diseases, dermal diseases, bullous skin diseases, pemphigus vulgaris, bullous pemphigoid and pemphigus foliaceus.

Examples of delayed type hypersensitivity include, but are not limited to, contact dermatitis and drug eruption.

Examples of types of T lymphocyte mediating hypersensitivity include, but are not limited to, helper T lymphocytes and cytotoxic T lymphocytes.

Examples of helper T lymphocyte-mediated hypersensitivity include, but are not limited to, $T_h1$ lymphocyte mediated hypersensitivity and $T_h2$ lymphocyte mediated hypersensitivity.

Autoimmune Diseases

Include, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), Wegener's granulomatosis, Takayasu's arteritis, Kawasaki syndrome (Praprotnik S. et al., Wien Klin Wochenschr 2000 Aug. 25; 112 (15-16):660), anti-factor VIII autoimmune disease (Lacroix-Desmazes S. et al., Semin Thromb Hemost. 2000; 26 (2): 157), necrotizing small vessel vasculitis, microscopic polyangiitis, Churg and Strauss syndrome, pauci-immune focal necrotizing and crescentic glomerulonephritis (Noel LH. Ann Med Interne (Paris). 2000 May; 151 (3): 178), antiphospholipid syndrome (Flamholz R. et al., J Clin Apheresis 1999; 14 (4):171), antibody-induced heart failure (Wallukat G. et al., Am J. Cardiol. 1999 Jun. 17; 83 (12A): 75H), thrombocytopenic purpura (Moccia F. Ann Ital Med. Int. 1999 April-June; 14 (2):114; Semple J W. et al., Blood 1996 May 15; 87 (10):4245), autoimmune hemolytic anemia (Efremov D G. et al., Leuk Lymphoma 1998 January; 28 (3-4):285; Sallah S. et al., Arm Hematol 1997 March; 74 (3):139), cardiac autoimmunity in Chagas' disease (Cunha-Neto E. et al., J Clin Invest 1996 Oct. 15; 98 (8):1709) and anti-helper T lymphocyte autoimmunity (Caporossi A P. et al., Viral Immunol 1998; 11 (1):9).

Examples of autoimmune rheumatoid diseases include, but are not limited to rheumatoid arthritis (Krenn V. et al., Histol Histopathol 2000 July; 15 (3):791; Tisch R, McDevitt H O. Proc Natl Acad Sci units S A 1994 Jan. 18; 91 (2):437) and ankylosing spondylitis (Jan Voswinkel et al., Arthritis Res 2001; 3 (3): 189).

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome. diseases include, but are not limited to autoimmune diseases of the pancreas, Type 1 diabetes (Castano L. and Eisenbarth G S. Ann. Rev. Immunol. 8:647; Zimmet P. Diabetes Res Clin Pract 1996 October; 34 Suppl: S125), autoimmune thyroid diseases, Graves' disease (Orgiazzi J. Endocrinol Metab Clin North Am 2000 June; 29 (2):339; Sakata S. et al., Mol Cell Endocrinol 1993 March; 92 (1):77), spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), idiopathic myxedema (Mitsuma T. Nippon Rinsho. 1999 August; 57 (8):1759), ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), autoimmune prostatitis (Alexander R B. et al., Urology 1997 December; 50 (6):893) and Type I autoimmune polyglandular syndrome (Hara T. et al., Blood. 1991 Mar. 1; 77 (5):1127).

Examples of autoimmune gastrointestinal diseases include, but are not limited to, chronic inflammatory intestinal diseases (Garcia Herola A. et al., Gastroenterol Hepatol. 2000 January; 23 (1):16), celiac disease (Landau Y E. and Shoenfeld Y. Harefuah 2000 Jan. 16; 138 (2):122), colitis, ileitis and Crohn's disease.

Examples of autoimmune cutaneous diseases include, but are not limited to, autoimmune bullous skin diseases, such as, but are not limited to, pemphigus vulgaris, bullous pemphigoid and pemphigus foliaceus.

Examples of autoimmune hepatic diseases include, but are not limited to, hepatitis, autoimmune chronic active hepatitis (Franco A. et al., Clin Immunol Immunopathol 1990 March; 54 (3):382), primary biliary cirrhosis (Jones D E. Clin Sci (Colch) 1996 November; 91 (5):551; Strassburg C P. et al., Eur J Gastroenterol Hepatol. 1999 June; 11 (6):595) and autoimmune hepatitis (Manns MP. J Hepatol 2000 August; 33 (2):326).

Examples of autoimmune neurological diseases include, but are not limited to, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83; Oshima M. et al., Eur J Immunol 1990 December; 20 (12):2563), neuropathies, motor neuropathies (Kornberg A J. J Clin Neurosci. 2000 May; 7 (3):191); Guillain-Barre syndrome and autoimmune neuropathies (Kusunoki S. Am J Med. Sci. 2000 April; 319 (4):234), myasthenia, Lambert-Eaton myasthenic syndrome (Takamori M. Am J Med. Sci. 2000 April; 319 (4):204); paraneoplastic neurological diseases, cerebellar atrophy, paraneoplastic cerebellar atrophy and stiff-man syndrome (Hiemstra H S. et al., Proc Natl Acad Sci units S A 2001 Mar. 27; 98 (7):3988); non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies (Antoine J C. and Honnorat J. Rev Neurol (Paris) 2000 January; 156 (1):23); dysimmune neuropathies (Nobile-Orazio E. et al., Electroencephalogr Clin Neurophysiol Suppl 1999; 50:419); acquired neuromyotonia, arthrogryposis multiplex congenita (Vincent A. et al., Ann N Y Acad. Sci. 1998 May 13; 841:482), neuritis, optic neuritis (Soderstrom M. et al., J Neurol Neurosurg Psychiatry 1994 May; 57 (5):544) and neurodegenerative diseases.

Examples of autoimmune muscular diseases include, but are not limited to, myositis, autoimmune myositis and primary Sjogren's syndrome (Feist E. et al., Int Arch Allergy Immunol 2000 September; 123 (1):92) and smooth muscle autoimmune disease (Zauli D. et al., Biomed Pharmacother 1999 June; 53 (5-6):234).

Examples of autoimmune nephric diseases include, but are not limited to, nephritis and autoimmune interstitial nephritis (Kelly CJ. J Am Soc Nephrol 1990 August; 1 (2):140).

Examples of autoimmune diseases related to reproduction include, but are not limited to, repeated fetal loss (Tincani A. et al., Lupus 1998; 7 Suppl 2:S107-9).

Examples of autoimmune connective tissue diseases include, but are not limited to, ear diseases, autoimmune ear diseases (Yoo T J. et al., Cell Immunol 1994 August; 157 (1):249) and autoimmune diseases of the inner ear (Gloddek B. et al., Ann N Y Acad Sci 1997 Dec. 29; 830:266).

Examples of autoimmune systemic diseases include, but are not limited to, systemic lupus erythematosus (Erikson J. et al., Immunol Res 1998; 17 (1-2):49) and systemic sclerosis (Renaudineau Y. et al., Clin Diagn Lab Immunol. 1999 March; 6 (2):156); Chan O T. et al., Immunol Rev 1999 June; 169:107).

Infectious Diseases

Examples of infectious diseases include, but are not limited to, chronic infectious diseases, subacute infectious diseases, acute infectious diseases, viral diseases, bacterial diseases, protozoan diseases, parasitic diseases, fungal diseases, mycoplasma diseases and prion diseases.

Graft Rejection Diseases

Examples of diseases associated with transplantation of a graft include, but are not limited to, graft rejection, chronic graft rejection, subacute graft rejection, hyperacute graft rejection, acute graft rejection and graft versus host disease.

Allergic Diseases

Examples of allergic diseases include, but are not limited to, asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

Cancerous Diseases

Examples of cancer include but are not limited to carcinoma, lymphoma, blastoma, sarcoma, and leukemia. Particular examples of cancerous diseases but are not limited to: Myeloid leukemia such as Chronic myelogenous leukemia. Acute myelogenous leukemia with maturation. Acute promyelocytic leukemia, Acute nonlymphocytic leukemia with increased basophils, Acute monocytic leukemia. Acute myelomonocytic leukemia with eosinophilia; Malignant lymphoma, such as Birkitt's Non-Hodgkin's; Lymphoctyic leukemia, such as Acute lumphoblastic leukemia. Chronic lymphocytic leukemia; Myeloproliferative diseases, such as Solid tumors Benign Meningioma, Mixed tumors of salivary gland, Colonic adenomas; Adenocarcinomas, such as Small cell lung cancer, Kidney, Uterus, Prostate, Bladder, Ovary, Colon, Sarcomas, Liposarcoma, myxoid, Synovial sarcoma, Rhabdomyosarcoma (alveolar), Extraskeletel myxoid chonodrosarcoma, Ewing's tumor; other include Testicular and ovarian dysgerminoma, Retinoblastoma, Wilms' tumor, Neuroblastoma, Malignant melanoma, Mesothelioma, breast, skin, prostate, and ovarian.

The molecule of the present invention can be administered to the subject per se, or in a pharmaceutical composition where it is mixed with suitable carriers or excipients.

Thus, according to another aspect of the present invention, there is provided a pharmaceutical composition and a pharmaceutically acceptable carrier.

As used herein, a "pharmaceutical composition" refers to a preparation of one or more of the active ingredients described herein with other chemical components such as physiologically suitable carriers and excipients. The purpose of a pharmaceutical composition is to facilitate administration of a compound to an organism. Preferably, the pharmaceutical composition is not immunogenic.

As used herein, the term "active ingredient" refers to the molecule of the present invention accountable for the intended biological effect.

Hereinafter, the phrases "physiologically acceptable carrier" and "pharmaceutically acceptable carrier," which may be used interchangeably, refer to a carrier or a diluent that does not cause significant irritation to an organism and does not abrogate the biological activity and properties of the administered compound. An adjuvant is included under these phrases.

Thus for example, the pharmaceutically acceptable carrier of the present invention may comprise a lipoamine acid.

Alternatively, the pharmaceutically acceptable carrier used by the present invention may comprise an embedding material such as a polyol (i.e., a carbohydrate). Non-limiting examples of carbohydrates which are suitable for use as excipients include maltodextrin (e.g., Glucidex Roquette), trehalose (e.g., Trehalose Merck), cellobiose, glucose, fructose, maltulose, iso-maltulose, lactulose, maltose, gentobiose, lactose, isomaltose, maltitol (e.g., Maltisorb Roquette), lactitol, erythritol, palatinitol, xylitol, mannitol, sorbitol, dulcitol and ribitol, sucrose, raffinose, gentianose, planteose, verbascose, stachyose, melezitose, dextran and inositol.

Yet alternatively, the pharmaceutically acceptable carrier used by the present is a microsphere suitable for oral administration. For example, the microsphere can include a water insoluble matrix of organic material that is resistant to dissolution or acidic degradation at pH levels found in the stomach (e.g., a pH level lower than 4) essentially as described in U.S. Pat. No. 6,849,271 to Vaghefi, et al., which is fully incorporated herein by reference. Such organic matrix material can be, for example, triglyceride, hydrogenated vegetable oil, a wax or a mixture of waxes, polyalkoxyalkylether, polyalkoxyalkylester and water insoluble partially degraded proteins.

It will be appreciated that the bioconjugated polymer (e.g., the PEGylated CCR5 peptide of the present invention) can be used in, and as a part of, the pharmaceutically acceptable carrier, and thus serves as a carrier molecule for delivery of the CCR5 amino acid sequence, while at the same time serving as a component of the delivery vehicle. A preferred embodiment of this dual use is a liposomal vehicle, e.g., PEG-conjugated liposomes, as described e.g., in U.S. Pat. Appl. No. 20030186869 to Poiani, George et al., which is fully incorporated herein by reference.

Herein, the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils, and polyethylene glycols.

Techniques for formulation and administration of drugs may be found in the latest edition of "Remington's Pharmaceutical Sciences," Mack Publishing Co., Easton, Pa., which is herein fully incorporated by reference.

Suitable routes of administration may, for example, include oral, rectal, transmucosal, especially transnasal, intestinal, or parenteral delivery, including intramuscular, subcutaneous, and intramedullary injections, as well as intrathecal, direct intraventricular, intravenous, inrtaperitoneal, intranasal, or intraocular injections.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping, or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations that can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries as desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, and sodium carbomethylcellulose; and/or physiologically acceptable polymers such as polyvinylpyrrolidone (PVP). If desired, disintegrating agents, such as cross-linked polyvinyl pyrrolidone, agar, or alginic acid or a salt thereof, such as sodium alginate, may be added.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions that can be used orally include push-fit capsules made of gelatin, as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate, and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane, or carbon dioxide. In the case of a pressurized aerosol, the dosage may be determined by providing a valve to deliver a metered amount. Capsules and cartridges of, for example, gelatin for use in a dispenser may be formulated containing a powder mix of the compound and a suitable powder base, such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with, optionally, an added preservative. The compositions may be suspensions, solutions, or emulsions in oily or aqueous vehicles, and may contain formulatory agents such as suspending, stabilizing, and/or dispersing agents.

Pharmaceutical compositions for parenteral administration include aqueous solutions of the active preparation in water-soluble form. Additionally, suspensions of the active ingredients may be prepared as appropriate oily or water-based injection suspensions. Suitable lipophilic solvents or vehicles include fatty oils such as sesame oil, or synthetic fatty acid esters such as ethyl oleate, triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the active ingredients, to allow for the preparation of highly concentrated solutions.

Alternatively, the active ingredient may be in powder form for constitution with a suitable vehicle, e.g., a sterile, pyrogen-free, water-based solution, before use.

The pharmaceutical composition of the present invention may also be formulated in rectal compositions such as suppositories or retention enemas, using, for example, conventional suppository bases such as cocoa butter or other glycerides.

Pharmaceutical compositions suitable for use in the context of the present invention include compositions wherein the active ingredients are contained in an amount effective to achieve the intended purpose. More specifically, a "therapeutically effective amount" means an amount of active ingredients (e.g., a nucleic acid construct) effective to prevent, alleviate, or ameliorate symptoms of a disorder (e.g., ischemia) or prolong the survival of the subject being treated.

Determination of a therapeutically effective amount is well within the capability of those skilled in the art, especially in light of the detailed disclosure provided herein.

For any preparation used in the methods of the invention, the dosage or the therapeutically effective amount can be estimated initially from in vitro and cell culture assays. For example, a dose can be formulated in animal models (see Examples 7, 9, 10 of the Examples section which follows) to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration, and dosage can be chosen by the individual physician in view of the patient's condition. (See, e.g., Fingl, E. et al. (1975), "The Pharmacological Basis of Therapeutics," Ch. 1, p. 1)

Dosage amount and administration intervals may be adjusted individually to provide sufficient plasma or brain levels of the active ingredient to induce or suppress the biological effect (i.e., minimally effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks, or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA-approved kit, which may contain one or more unit dosage forms containing the active ingredient. The pack may, for example, comprise metal or plastic foil, such as a blister pack. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising a preparation of the invention formulated in a pharmaceutically acceptable carrier may also be prepared, placed in an appropriate container, and labeled for treatment of an indicated condition, as further detailed above.

It will be appreciated that the molecule (e.g., chimeric proteinaceous) of this aspect of the present invention can be provided to the subject by means of gene therapy. Hence the above-described mammalian expression construct can be administered to the subject employing any suitable mode of administration, described hereinabove (i.e., in-vivo gene therapy). Alternatively, the nucleic acid construct is introduced into a suitable cell via an appropriate gene delivery vehicle/method (transfection, transduction, homologous recombination, etc.) and an expression system as needed and then the modified cells are expanded in culture and returned to the subject (i.e., ex-vivo gene therapy).

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. Preferably the signal sequence for this purpose is a mammalian signal sequence such as the Igκ leader sequence (e.g., SEQ ID NOs. 3). Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

The affinity of the CCR5 peptide of the present invention to CCR5 ligands allows use thereof in purification and detection of CCR5 ligands.

Thus, according to another aspect of the present invention, there is provided a molecule comprising a tag attached to a CCR5 amino acid sequence devoid of an N-terminus domain of CCR5, the CCR5 amino acid sequence being capable of binding a CCR5 ligand.

As used herein the term "tag" refers to a moiety which is specifically recognized by a binding partner such as an antibody, a chelator or an avidin (biotin) molecule. The tag can be placed C-terminally or N-terminally of the CCR5 peptide, as long as it does not interfere with a biological activity thereof (e.g., ligand binding).

For example, a tag polypeptide has enough residues to provide an epitope (i.e., epitope tag) against which an antibody thereagainst can be made, yet is short enough such that it does not interfere with biological activity of the CCR5 peptide. The epitope tag preferably also is fairly unique so that the antibody thereagainst does not substantially cross-react with other epitopes. Suitable tag polypeptides generally have at least six amino acid residues and usually between about 8-50 amino acid residues (preferably between about 9-30 residues). Preferred are poly-histidine sequences, which bind nickel, allowing isolation of the tagged protein by Ni-NTA chromatography as described (Lindsay et al. Neuron 17:571-574 (1996)], for example.

Such epitope-tagged forms of the CCR5 are desirable, as the presence thereof can be detected using a labeled antibody against the tag polypeptide. Also, provision of the epitope tag enables the CCR5 peptide of the present invention to be readily purified by affinity purification using the anti-tag antibody. Affinity purification techniques and diagnostic assays involving antibodies are described later herein.

Tag polypeptides and their respective antibodies are well known in the art. Examples include the flu HA tag polypeptide and its antibody 12CA5 (Field et al., Mol. Cell. Biol., 8:2159-2165 (1988)]; the c-myc tag and the 8F9, 3C7, 6E10, G4, B7 and 9E10 antibodies thereto (Evan et al., Molecular and Cellular Biology, 5:3610-3616 (1985)]; and the Herpes Simplex virus glycoprotein D (gD) tag and its antibody. Paborsky et al., Protein Engineering, 3(6):547-553 (1990). Other tag polypeptides have been disclosed. Examples include the Flag-peptide [Hopp et al., BioTechnology, 6:1204-1210 (1988)]; the KT3 epitope peptide [Martin et al., Science, 255:192-194 (1992)]; an α-tubulin epitope peptide [Skinner et al., J. Biol. Chem., 266:15163-15166 (1991)]; and the T7 gene 10 protein peptide tag [Lutz-Freyermuth et al., Proc. Natl. Acad. Sci. USA, 87:6393-6397 (1990)]. Once the tag polypeptide has been selected, an antibody thereto can be generated using methods which are well known in the art. Such antibodies are commercially available such as from Sigma, St. Louis. USA.

According to an embodiment of this aspect of the present invention, there is provided a method of isolating a CCR5 ligand from a biological sample or detecting the presence of CCR5 ligands therein.

As used herein the phrase "biological sample" refers to a biological material, such as cells, tissues and fluids such as blood, serum, plasma, lymph, bile fluid, urine, saliva, sputum, synovial fluid, semen, tears, cerebrospinal fluid, bronchioalveolar large fluid, ascites fluid, pus, conditioned medium and the like in which CCR5 ligands is present.

Isolation of CCR5 ligands according to this aspect of the present invention is effected by contacting the biological sample with the molecule of this aspect of the present invention, such that CCR5 ligands and the molecule form a complex (using buffer, temperature conditions which allow binding of the molecule to CCR5 ligands, see for Example Datta-Mannan and Stone 2004, supra); and isolating the complex to thereby isolate CCR5 ligands from the biological sample.

In order to isolate the complex, the molecule is preferably immobilized on a solid support. As used herein the phrase "solid support" refers to a non-aqueous matrix to which a reagent of interest (e.g., the molecule of this aspect of the present invention) can adhere. Examples of solid supports, include, but are not limited to, solid supports formed partially or entirely of glass (e.g., controlled pore glass), polysaccharides (e.g., agarose), polyacrylamides, polystyrene, polyvinyl alcohol and silicones. In certain embodiments, depending on the context, the solid support can comprise the well of an assay plate; in others it is a purification column (e.g., an affinity chromatography column). This term also includes a discontinuous solid phase of discrete particles, such as those described in U.S. Pat. No. 4,275,149.

Alternatively, such molecules can be used to detect the levels of CCR5 ligands in biological samples. For diagnostic applications, molecules typically will be labeled with a detectable moiety. The detectable moiety can be any one which is capable of producing, either directly or indirectly, a detectable signal. For example, the detectable moiety may be a radioisotope, a fluorescent or chemiluminescent compound, or a tag (such as described hereinabove and to which a labeled antibody can bind). The molecules of the present invention may be employed in any known assay method, such as competitive binding assays, direct and indirect sandwich assays, and immunoprecipitation assays. [Zola, Monoclonal Antibodies: A Manual of Techniques, pp. 147-158 (CRC Press, Inc., 1987)].

The molecules of this aspect of the present invention can be included in a diagnostic kit, in which the molecule and optionally solid support and imaging reagents (e.g., antibodies, chromogenic substrate etc.) can be packaged in suitable containers with appropriate buffers and preservatives and used for diagnosis.

Thus, the present invention provides for molecules, compositions and clinical methods of using same such as in diagnostics and therapy.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Generation of Recombinant Human and Murine CCR5-Fc Fusion Protein (CCR5-Ig) and Stable Expression in Cell Lines Recombinant human (h) or murine (m) CCR5-Ig fusion proteins were produced for therapeutic use.

Materials and Experimental Procedures

Generation of Human CCR5-Ig Construct

Figure 1:
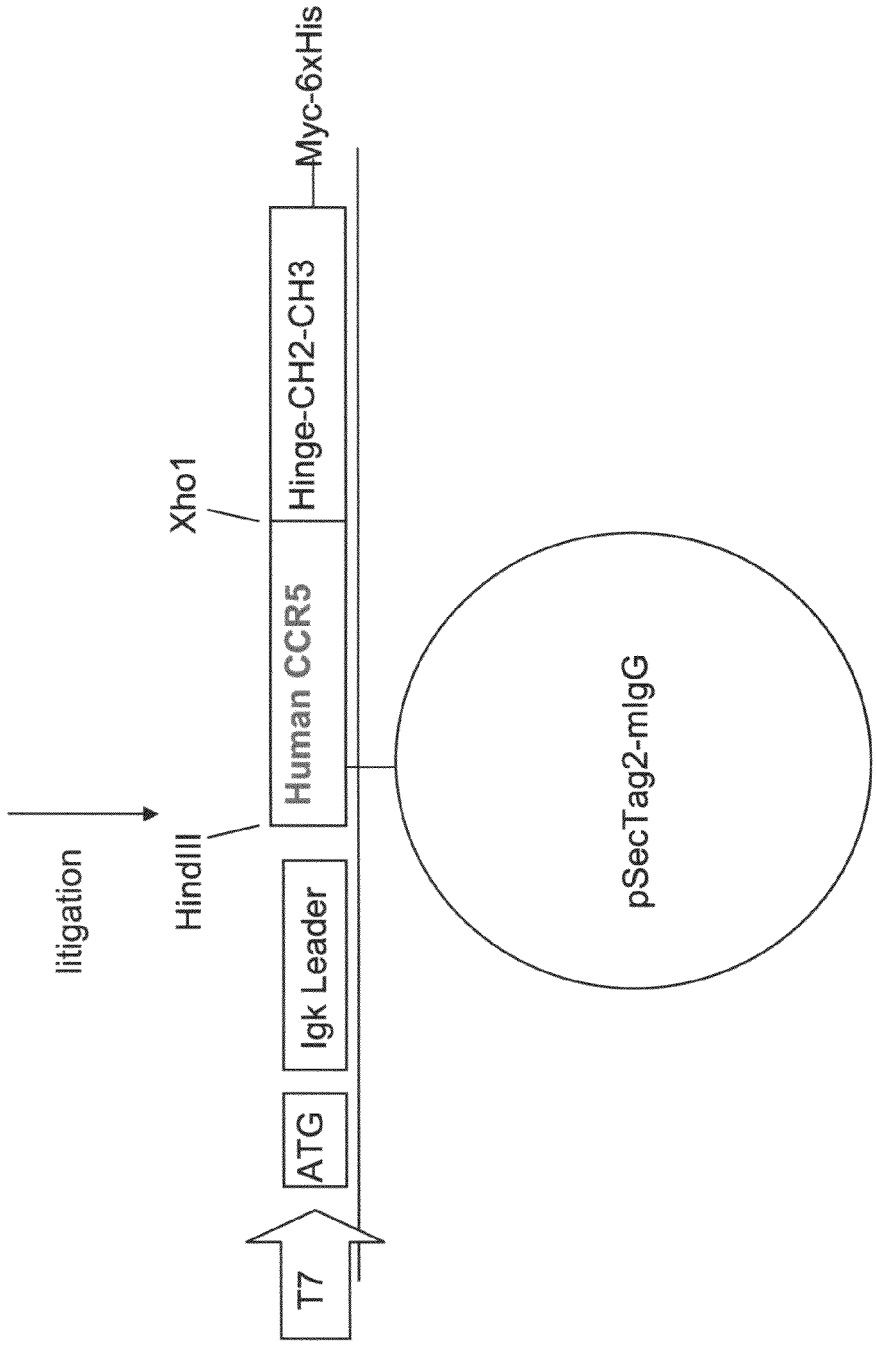

Construction of the nucleic acid vector encoding the CCR5-Ig fusion protein of the present invention is schematically illustrated in FIG. 1. The IgG 1 construct was produced according to the basic protocol that was previously utilized for the generation of CTLA4-Ig [Van Oosterhout et al., Am J Respir Cell Mol Biol (1997) 17:386] with the following modifications: cDNA encoding the constant region (Hinge- CH2-CH3) of human IgG1 heavy chain has been cloned from LPS and IL-4 activated peripheral blood mononuclear cells (PBMC) onto pSecTag2/Hygro B (Invitrogen, San Diego, Calif.). Human CCR5 (GenBank Accession No. NM_000579, SEQ ID NO: 33) was subcloned from LPS activated human PBMC using primers complementary to the extracellular 2 (EC2 nucleic acid coordinates 493-585 of CCR5; SEQ ID NO: 17) domain of the receptor as follows: Sense, cccaagcttaccagatctcaaaaagaagg (SEQ ID NO. 35), Antisense: ccgctcgagattcttccagaattgatact (SEQ ID NO. 36). Following sequence verification the amplified PCR product was cloned into a pSec-Tag2 vector (Invitrogen, San Diego, Calif.). Hinge-CH2-CH3 (SEQ ID NO: 21) of the human IgG Fcγ was ligated to the plasmid (pSec-CCR5) downstream of the CCR5 to create a fusion protein hCCR5(EC2)-IgG (SEQ ID NO. 4).

Generation of Murine CCR5-Ig Construct

Murine CCR5 (GenBank Accession No. NM_009917) was subcloned from LPS activated murine PBMC using primers complementary to the different extracellular domains: extracellular 1 (E1 or EC1 amino acid coordinates 271-336 of CCR5; SEQ ID NO: 7) domain of the receptor as follow: Sense, cccaagctttatgctgcaaatgagtgggt (SEQ ID NO. 39), Antisense: ccgctcgagaatgtgatagagccctgtga (SEQ ID NO. 40); extracellular 2 (E2 or EC2 amino acid coordinates 508-597 of CCR5; SEQ ID NO: 9) domain of the receptor as follow: Sense, cccaagcttagatctcagaaagaaggttt (SEQ ID NO. 31), Antisense: ccgctcgagctttaatgtttggaaactct (SEQ ID NO. 32); the extracellular 3 (E3 or EC3 amino acid coordinates 790-864 of CCR5; SEQ ID NO: 11) domain of the receptor as follow: Sense, cccaagcttgaattctttggactgaataa (SEQ ID NO. 41), Antisense: ccgctcgagcattccaagagtctctgttg (SEQ ID NO. 42); and N-terminus (N amino acid coordinates 1-81 of CCR5; SEQ ID NO: 5) domain of the receptor as follow: Sense, cccaagcttatggattttcaagggtcagt (SEQ ID NO. 37), Antisense: ccgctcgagcacattgattttttggcagg (SEQ ID NO. 38). Following sequence verification the amplified PCR product was cloned into a pSec-Tag2 vector (Invitrogen, San Diego, Calif.). Hinge-CH2-CH3 (SEQ ID NO: 25) of the murine IgG Fcγ was ligated to the plasmid (pSec-CCR5) down stream of the CCR5 to create a fusion protein mCCR5(EC2)-IgG (SEQ ID NO: 2).

Generation of Stable human CCR5-IgG-Expressing Cell Lines

The pSec-CCR5-IgG plasmid was co-transfected into DG44 Chinese hamster ovary (CHO) cells that have a double deletion for the dihydrofolate reductase (DHFR) gene (DG44 CHO DHFR$^{-/-}$ cells, provided by Dr. Lawrence Chasin from Columbia university, USA, ATCC Accession No. CRL-9096), with CHO DHFR minigene vector, which transfects DHFR-deficient CHO cells with high efficiency, using jetPEI (Polypluse transfection—Illkirch Cedex, France) according the manufacturer's protocol. Stably transfected cells were selected in a culture medium (MEM-alpha) containing hygromycine (200 µg/ml) and increasing doses of methotrixate (2.5 nM to 0.1 mM). The hCCR5(EC2)-IgG fusion protein was purified from DHFR-positive transfectant supernatants by a protein A-Sepharose column obtained from Amersham Biosciences (Uppsia, Sweden) and verified by western blot analysis using mouse anti myc (Santa cruz lot no. d0306) as primary antibody and goat anti mouse IgG-HRP (Jackson ImmunoResearch lot no. 58734) as secondary antibody.

Generation of Stable murine CCR5-IgG-Expressing Cell Lines

The pSec-CCR5-IgG plasmid was co-transfected into DG44 Chinese hamster ovary (CHO) cells that have a double deletion for the dihydrofolate reductase (DHFR) gene (DG44 CHO DHFR$^{-/-}$ cells, provided by Dr. Lawrence Chasin from Columbia university, USA, ATCC Accession No. CRL-9096), with CHO DHFR minigene vector, which transfects DHFR-deficient CHO cells with high efficiency, using jetPEI (Polypluse transfection —Illkirch Cedex, France) according the manufacturer's protocol. Stably transfected cells were selected in a culture medium (MEM-alpha) containing hygromycine (200 µg/ml) and increasing doses of methotrixate (2.5 nM to 0.1 mM). The mCCR5(EC2)-IgG fusion protein was purified from DHFR-positive transfectant supernatants by a protein A-Sepharose column obtained from Amersham Biosciences (Uppsia, Sweden) and verified by western blot analysis using mouse anti myc (Santa cruz lot no. d0306) as primary antibody and goat anti mouse IgG-HRP (Jackson ImmunoResearch lot no. 58734) secondary antibody.

Example 2

Binding Characteristics of the Different CCR5-IgG Extracellular Domains to CCR5 Ligands The ability of EC1, EC2, EC3 and N domains of mCCR5-Ig to bind specifically to CCR5 natural ligands (CCL3, CCL4 and CCL5) was addressed by an ELISA assay.

Materials and Experimental Procedures

ELISA

The binding specificity of the different extracellular domains (EC1, EC2, EC3 and N) of the murine CCR5-IgG fusion proteins to various commercially available murine recombinant C—C chemokines (R&D Systems, Minneapolis, N. Mex. including MIP-1α (CCL3), (CCL4) and RANTES (CCL5) was determined by direct ELISA as follows: 96-well ELISA plates (Nunc, Roskilde, Denmark) were coated with 10 ng/well of murine CCL3, CCL4 or CCR5 and blocked with 1% BSA in PBS. Wells were washed and incubated with 10 ng/ml, 100 ng/ml or 1000 ng/ml CCR5-IgG (EC1, EC2, EC3, N) at a concentration overnight. Wells were washed and the presence of CCR5-IgG was detected with goat anti mouse IgG-HRP (Jackson ImmunoResearch lot no. 58734). Results are shown as O.D. reading at 450 nm.

Results

Binding of the EC I, EC2, EC3 and N domains of mCCR5-IgG to CCR5 natural ligands (CCL3, CCL4 and CCL5) was determined by a direct ELISA. As shown in FIGS. 2A-C, only mCCR5(EC2)-IgG bound specifically to all three ligands, while mCCR5(EC1)-IgG and mCCR5(N)-IgG did not bind neither of the ligands. At high protein concentration (1000 ng), mCCR5(EC2)-IgG also bound the ligands to some extent.

Example 3 mCCR5(EC2)-IgG Selectively Binds CCL3, CCL4 and CCL5

The ability of the soluble receptor mCCR5(EC2)-IgG to bind different chemokines was addressed by an ELISA assay.

Materials and Experimental Procedures

ELISA

The binding specificity of the murine CCR5-IgG soluble receptor to various commercially available murine recombinant chemokines (R&D Systems, Minneapolis, N. Mex. including MIP-1α (CCL3), MIP-1β (CCL4), RANTES (CCL5), ITAC, MCP-1 (CCL2), CXCL16, MIG and IL-4 was determined by direct ELISA as follows: 96-well ELISA plates (Nunc, Roskilde, Denmark) were coated with 10 ng/well of murine CCL3, CCL4, CCL5, ITAC, MCP-1, CXCL16, MIG or IL-4 and blocked with 1% BSA in PBS. Wells were washed and incubated with 1 µg/well CCR5 (EC2)-IgG overnight. Wells were washed and the presence of CCR5(EC2)-IgG was detected with goat anti mouse IgG-HRP (Jackson ImmunoResearch lot no. 58734). Results are shown as O.D. reading at 450 nm.

Results

Binding of mCCR5(EC2)-IgG to different chemokines confirmed the specificity of mCCR5(EC2)-IgG to its natural ligands. As illustrated in FIGS. 3A-B, mCCR5(EC2)-IgG bound with high affinity to CCL5 (FIGS. 3A-B) as well as to CCL3 and CCL4 (FIG. 3B). Some insignificant, low affinity binding of mCCR5(EC2)-IgG to MCP-1 and CXCL16 was detected at higher protein concentration (1000 ng, FIGS. 3A-B).

Example 4

Cross Reactivity Between mCCR5(EC2)-IgG and Human CCL3, CCL4 and CCL5

The ability of the soluble receptor mCCR5(EC2)-IgG to bind human C—C chemokines was addressed by an ELISA assay.

Materials and Experimental Procedures
ELISA

The binding specificity of the murine CCR5-IgG soluble receptor to various commercially available human recombinant chemokines (R&D Systems, Minneapolis, N. Mex.) MIP-1α (CCL3), MIP-1β (CCL4) and RANTES as well as the murine recombinant chemokines (R&D Systems, Minneapolis, N. Mex.) MIP-1α (CCL3) and ITAC was determined by direct ELISA as follows: 96-well ELISA plates (Nunc, Roskilde, Denmark) were coated with 10 ng/well of human CCL3, CCL4, CCL5, as well as murine CCL3 or ITAC, and blocked with 1% BSA in PBS. Wells were washed and incubated with 1 µg/well CCR5(EC2)-IgG overnight. Wells were washed and the presence of CCR5(EC2)-IgG was detected with goat anti mouse IgG-HRP antibody (Jackson ImmunoResearch lot no. 58734). Results are shown as O.D. reading at 450 nm.

Results

As illustrated in FIG. 4, mCCR5(EC2)-IgG bound to human CCL3, CCL4 and CCL5 with high affinity. There was no marked difference between murine or human ligand binding of the murine soluble receptor CCR5(EC2)-IgG.

Example 5 mCCR5(EC2)-IgG Neutralizes CCR5-Ligand-Induced Cell Migration

The ability of EC2, EC3 or N domains of the murine CCR5-Ig to specifically neutralize CCL3, CCL4 and CCL5 induced cell migration was addressed by a chemotaxis assay.

Materials and Experimental Procedures
Cell Lines

THP-1 cells (Human acute monocytic leukemia cell line), expressing CCR5 and CCR2, were obtained from American Type Culture Collection (ATCC, Rockville, Md. with ATCC Accession No. TIB-202) and grown according to the manufacturers protocol.

Cell Migration Assay

The ability of mCCR5(EC2, EC3 and N)-IgG to inhibit murine CCL3, CCL4 and CCL5 induced migration of THP-1 cells was tested. Chemotaxis assays were conducted using a TransWell chamber (Corning Costar, Cambridge, Mass.). Transwells were incubated for 30 minutes with 15 ng/well murine CCL3, 10 ng/well murine CCL4 and 50 ng/well murine CCL5 (R&D Systems, Minneapolis, N. Mex.) along with 10 µg/well of the different mCCR5-IgG extracellular domains (as stated above). THP-1 cells were starved for 24 hours in culture free medium (RPMI containing L-Glu, Na-Pyr and pen.-strep.) and were laid ($1\times10^6$ cells/well) in the upper chamber of the Transwells. Transwells were then incubated for 3 hours at 37° C. in humidified air containing 7.5% $CO_2$. Migrating monocytes were collected from the lower chamber and counted by FACS.

Results

FIGS. 5A-C shows that the soluble receptor mCCR5 (EC2)-IgG inhibited substantially all THP-1 migration induced by CCL3 (FIG. 5A), CCL4 (FIG. 5B) and CCL5 (FIG. 5C). Additionally, mCCR5(EC3)-IgG substantially inhibited THP-1 migration induced by CCL4 and CCL5 (by about 50%), yet mCCR5(N)-IgG did not inhibit cell migration induced by chemokines.

Example 6 hCCR5(EC2)-IgG Neutralizes CCL3-Induced Cell Migration

The ability of the fusion protein hCCR5(EC2)-Ig to specifically neutralize CCL3 induced cell migration was addressed by a chemotaxis assay.

Materials and Experimental Procedures
Cell Lines

THP-1 cells (Human acute monocytic leukemia cell line), expressing CCR5 and CCR2, were obtained from American Type Culture Collection (ATCC, Rockville, Md. with ATCC Accession No. TIB-202) and grown according to the manufacturers protocol.

Cell Migration Assay

The ability of hCCR5(EC2)-IgG to inhibit CCL3 induced migration of THP-1 cells was tested. Chemotaxis assays were conducted using a TransWell chamber (Corning Costar, Cambridge, Mass.). THP-1 cells with medium ($1\times10^6$ cells/well) were added to the upper chamber of the Transwell, after equilibration of the lower chambers with medium or with recombinant human MIP-1α (CCL3, R&D Systems, Minneapolis, N. Mex.), that were, or were not, supplemented with the soluble hCCR5(EC2)-IgG 200 ng/well. To assess chemokine specificity, MCP-1 (CCL2, R&D Systems, Minneapolis, N. Mex.) was used as a control. Transwells were then incubated for 3 hours at 37° C. in humidified air containing 7.5% $CO_2$. Migrating monocytes were collected from the lower chamber and counted.

Results

FIG. 6 shows that the soluble receptor hCCR5(EC2)-IgG significantly (50%) and selectively inhibited migration of THP-1 cells induced by MIP-1α (CCL3) and not by MCP-1 (CCL2, $p<0.001$).

Example 7

CCR5(EC2)-IgG Suppresses ongoing Experimental Autoimmune Encephalomyelitis

The EC2 domain of the murine soluble receptor CCR5-Ig was shown highly effective in suppressing ongoing Experimental Autoimmune Encephalomyelitis (EAE) in mice, an animal model for multiple sclerosis (MS).

Materials and Experimental Procedures

Induction of EAE in Mice and Suppression of the Ongoing Disease with CCR5(EC2)-IgG.

Three groups of C57/B mice (4 mice in each group) were subjected to active induction of EAE by MOGp35-55 (myelin oligodendrocyte glycoprotein) as was previously described [Kassiotis and Kollias, J Exp Med (2001) 193(4):427-434]. Beginning one day after the onset of disease (day 12), these mice were treated with repeated intravenous administrations (every other day) of 300 μg/mouse of either a CCR5(EC2)-IgG, isotype matched IgG or with PBS. An observer blind to the experimental procedure scored EAE daily for clinical manifestation of disease.

Results

Administration of EC2 domain of mCCR5-IgG to EAE mice initiated EAE remission without residual sign of disease while mice treated with PBS or control IgG developed severe EAE (FIG. 7).

Example 8

CCR5(EC2)-IgG Alters the Cytokine Profile of Primary EAE Response In-Vitro

The ability of the murine soluble receptor CCR5-Ig to alter in-vitro cytokine secretion by EAE splenocytes was analyzed.

Materials and Experimental Procedures

Induction of EAE in Mice and EAE Splenocyte Reactivation In Vitro for Cytokine Production.

Three groups of C57/B mice (4 mice in each group) were subjected to active induction of EAE by MOGp35-55 (myelin oligodendrocyte glycoprotein) as was previously described [Kassiotis and Kollias, J Exp Med (2001) 193(4):427-434]. On day 9 the splenocytes were harvested and were restimulated for 72 hours with 50 μg/ml MOGp35-55 along with different concentrations of isotype matched IgG (mIgG), control CCR5 [CCR5(EC3)-IgG] or CCR5(EC2)-IgG. The supernatants were analyzed by ELISA for cytokine production The ELISA was performed using Eli-pair kits (Diaclone, Fleming, France) according to the protocol.

Results

Stimulation of antigen specific primary cultures (EAE-derived splenocytes) by CCR5-Ig(E2) markedly suppressed TNF-α' production (FIG. 8A) and significantly reduces in-vitro IL-12 production (p<0.01, FIG. 8C). However, CCR5-Ig(E2) did not influence IFN-γ production (FIG. 8B). Stimulation by isotype matched IgG or control mCCR5(EC3)-IgG displayed high levels of cytokine secretion by EAE-derived splenocytes (FIGS. 8A-C). TNF-α and IL-12 are major inflammatory cytokine involved in inflammatory diseases, particularly in EAE. The marked reduction in TNF-α and IL-12 production by the use of CCR5-Ig(E2) points to a therapeutic effect.

Example 9

CCR5(EC2)-IgG is Capable of Treating Type I Diabetes Mellitus as Demonstrated in NOD Mice The ability of EC2 domain of CCR5-Ig to treat Type 1 Diabetes Mellitus (TIDM) is determined in NOD mice, a well established animal model for the disease.

Materials and Experimental Procedures

Animals

Non-obese diabetic (NOD) mice develop spontaneous autoimmune diabetes and are commonly used as an experimental model for human insulin-dependent diabetes mellitus [Miazaki A., Clin. Exp. Immunol. (1998) 60:622; Harada, M., Exp. Clin. Endocrinol. (1987) 89:251]. Six to twelve week old NOD/Ltj female mice are fed standard laboratory animal chow ad libitum and are kept in Specific Pathogen Free (SPF) animal house facility.

Treatment of Mice with CCR5(EC2)-IgG

Three groups of six, 20 day old NOD mice are subcutaneously treated. The first group is subjected to repeated administrations of CCR5(EC2)-IgG (100 μg per mice per day). The second group is administered with a matching amount of PBS, and the third with isotype matched control IgG.

Results

Administration of EC2 domain of CCR5-IgG to NOD mice is expected to reduce insulitis (e.g., by pancreatic cell death assay). These findings support the use of the compositions of the present invention for treating T1DM.

Example 10

CCR5(EC2)-IgG is Capable of Treating Rheumatoid Arthritis

The EC2 domain of the human soluble receptor CCR5-Ig is shown highly effective in suppressing ongoing Adjuvant Induced Arthritis (AA), an animal model for Rheumatoid Arthritis (RA).

Materials and Experimental Procedures

Induction of Collagen-Induced Arthritis in Mice and Suppression of the Ongoing Disease with CCR5(EC2)-IgG In order to induce arthritis in mice, Male DBA/1 mice (8-12 weeks old) are injected intradermally at the base of the tail with 200 μg type II collagen purified from bovine articular cartilage and emulsified in complete Freund's adjuvant (CFA; Difco Laboratories, Detroit, Mich., USA) as described by Williams et. al. [Williams et. al., Proc Natl Acad Sci USA (1992) 89:9784-9788]. The mice receive a booster injection of 200 μg type II collagen emulsified in CFA, 3 weeks after the first dose. The mice are inspected daily and each animal with erythema and/or swelling in one or more limbs is randomly assigned to one of 3 groups, which receives intraperitoneal (i.p.) injections of CCR5(EC2)-IgG (100 μg per mice per day), isotype matched human IgG (IgG1), or PBS. Each mouse is injected on the day of disease onset (day 0) and then every other day for 10 days with 100 μg soluble receptor in 500 μl PBS. Arthritis is monitored over the 10 days treatment period by measuring paw swelling.

In order to measure paw swelling, the thickness of each affected hind paw is measured with microcalipers. The results are expressed as a direct measure of paw width in millimeters.

Results

Administration of EC2 domain of CCR5-IgG to AA mice is expected to moderate collagen-induced arthritis and thus to reduce paw swelling in treated mice compared to mice injected with PBS or IgG. These findings support the use of the compositions of the present invention for treating RA.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications and GenBank Accession numbers mentioned in this specification are herein incorporated in their entirety by reference into the specification, to the same extent as if each individual publication, patent or patent application or GenBank Accession number was specifically and individually indicated to be incorporated herein by reference. In addition, citation or identification of any reference in this application shall not be construed as an admission that such reference is available as prior art to the present invention.

What is claimed is:

1. An isolated molecule as set forth in SEQ ID NO: 2 or 4.

2. An isolated polynucleotide comprising a nucleic acid sequence encoding the molecule of claim 1.

3. A pharmaceutical composition comprising as an active ingredient the molecule of claim 1 and a pharmaceutically acceptable carrier.

4. The molecule of claim 1, attached to a non-protein moiety.

5. A method of treating multiple sclerosis in a subject in need thereof, the method comprising administering to the subject a therapeutically effective amount of the molecule of claim 1, thereby treating the subject.

* * * * *